(12) United States Patent
Decaux et al.

(10) Patent No.: US 10,667,985 B2
(45) Date of Patent: Jun. 2, 2020

(54) APPLICATOR AND CAPSULE FOR SUCH APPLICATOR

(71) Applicant: InDerm, Paris (FR)

(72) Inventors: Stéphane Decaux, Paris (FR); Géraldine Decaux, Paris (FR); Jean Luc Thuliez, Le Landeron (CH); Etienne Crozier, La Neuveville (CH); Guillaume Heisel, Lignières (CH)

(73) Assignee: ID Lab, Paris (FR)

( * ) Notice: Subject to any disclaimer, the term of this patent is extended or adjusted under 35 U.S.C. 154(b) by 1073 days.

(21) Appl. No.: 14/310,083

(22) Filed: Jun. 20, 2014

(65) Prior Publication Data

US 2015/0360014 A1   Dec. 17, 2015

Related U.S. Application Data

(60) Provisional application No. 62/012,568, filed on Jun. 16, 2014.

(51) Int. Cl.
*A61H 15/02* (2006.01)
*A61M 35/00* (2006.01)
(Continued)

(52) U.S. Cl.
CPC ............. *A61H 15/02* (2013.01); *A45D 34/00* (2013.01); *A45D 34/04* (2013.01); *A45D 34/041* (2013.01);
(Continued)

(58) Field of Classification Search
CPC ... A61M 35/003; A45D 34/04; A45D 34/041; A45D 2034/005; A61H 15/0085; A61H 15/002; A61N 5/06; A61N 2005/0644
See application file for complete search history.

(56) References Cited

U.S. PATENT DOCUMENTS

| 4,858,600 A | 8/1989 | Gross et al. |
| 5,553,957 A * | 9/1996 | Dornbusch ......... A45D 34/041 401/209 |

(Continued)

FOREIGN PATENT DOCUMENTS

| WO | 2010/111997 A2 | 10/2010 |
| WO | 2011/019788 A1 | 2/2011 |

(Continued)

OTHER PUBLICATIONS

International Search Report issued from corresponding PCT/EP2015/063462, dated Sep. 30, 2015.

*Primary Examiner* — Nathan R Price
*Assistant Examiner* — Melissa A Snyder
(74) *Attorney, Agent, or Firm* — Banner & Witcoff, Ltd.

(57) ABSTRACT

A device for distributing, on a surface of a living body, a product containing an active component or forming a cosmetic product, the device comprising a housing and a cartridge, releasably coupled to the housing, wherein:
the cartridge comprises an applicator element and a reservoir containing said product and having a movable or deformable wall part for reducing the volume of the reservoir, wherein at least one opening is provided between the reservoir and the applicator element for applying the product to the applicator element by reducing the volume of the reservoir; and
the housing comprises at least one light source for radiating light through and/or alongside the cartridge and a drive for driving the movable and/or deformable wall part of the reservoir for reducing the volume of the reservoir.

31 Claims, 36 Drawing Sheets

(51) Int. Cl.

| | |
|---|---|
| *A45D 34/04* | (2006.01) |
| *A61N 5/06* | (2006.01) |
| *A61H 15/00* | (2006.01) |
| *A61H 23/02* | (2006.01) |
| *A45D 34/00* | (2006.01) |
| *A61K 9/00* | (2006.01) |
| *A45D 40/26* | (2006.01) |
| *A61M 37/00* | (2006.01) |

(52) U.S. Cl.
CPC ....... *A45D 40/261* (2013.01); *A61H 15/0085* (2013.01); *A61H 23/0245* (2013.01); *A61H 23/0254* (2013.01); *A61K 9/00* (2013.01); *A61M 35/003* (2013.01); *A61N 5/06* (2013.01); *A61N 5/0616* (2013.01); *A45D 2034/005* (2013.01); *A45D 2200/205* (2013.01); *A61H 2015/0042* (2013.01); *A61H 2201/10* (2013.01); *A61H 2201/105* (2013.01); *A61H 2201/1215* (2013.01); *A61H 2201/1246* (2013.01); *A61M 2037/0007* (2013.01); *A61N 2005/0631* (2013.01); *A61N 2005/0644* (2013.01)

(56) References Cited

U.S. PATENT DOCUMENTS

| | | |
|---|---|---|
| 6,494,899 B1 | 12/2002 | Griffin et al. |
| 2004/0024336 A1 | 2/2004 | Lin |
| 2007/0038206 A1* | 2/2007 | Altshuler ........... A46B 15/0036 606/20 |
| 2008/0014011 A1 | 1/2008 | Rossen |
| 2008/0146977 A1 | 6/2008 | Hilditch |
| 2008/0262394 A1* | 10/2008 | Pryor ..................... A61H 7/007 601/15 |
| 2009/0299236 A1 | 12/2009 | Pryor et al. |
| 2012/0109041 A1* | 5/2012 | Munz .................. A45D 34/041 604/20 |
| 2012/0207532 A1 | 8/2012 | Ho |
| 2013/0101340 A1 | 4/2013 | Liu |
| 2015/0182002 A1* | 7/2015 | Hartstock-Martin ....................... A46B 11/0003 401/135 |

FOREIGN PATENT DOCUMENTS

| | | |
|---|---|---|
| WO | 2011/051941 A1 | 5/2011 |
| WO | 2014/091035 A1 | 6/2014 |

* cited by examiner

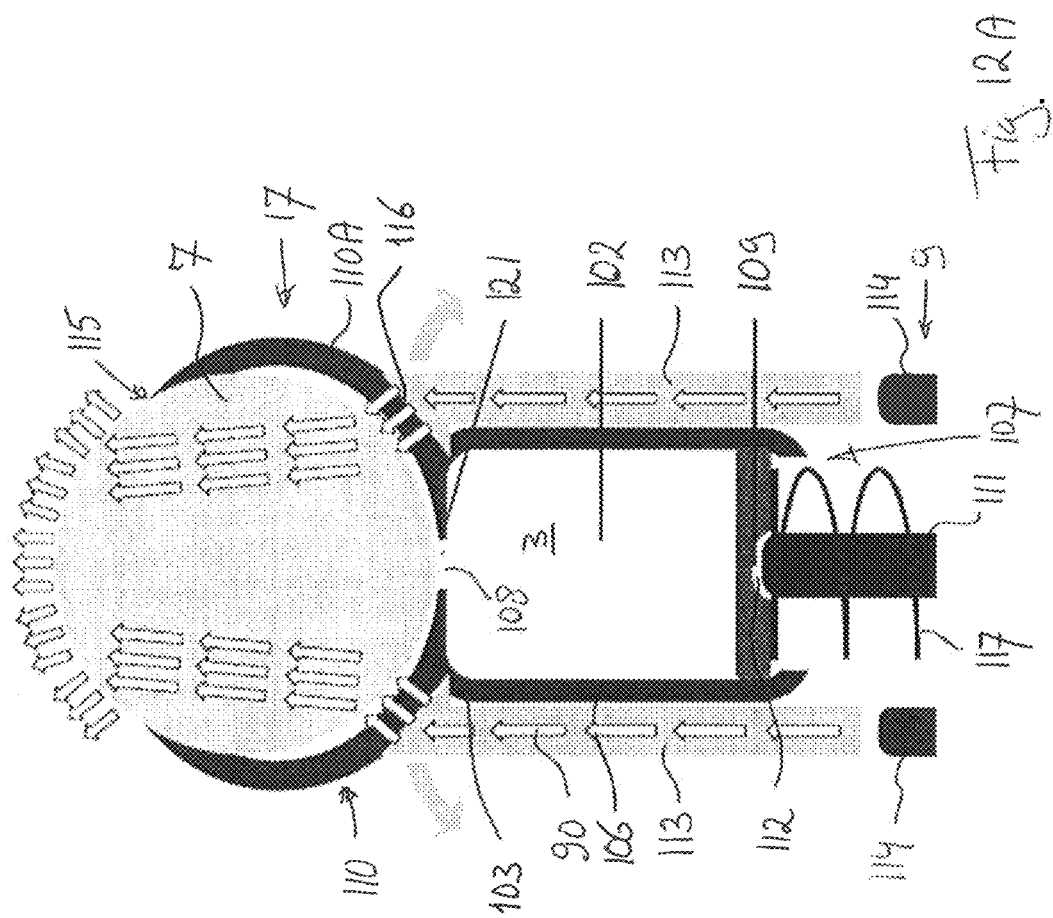

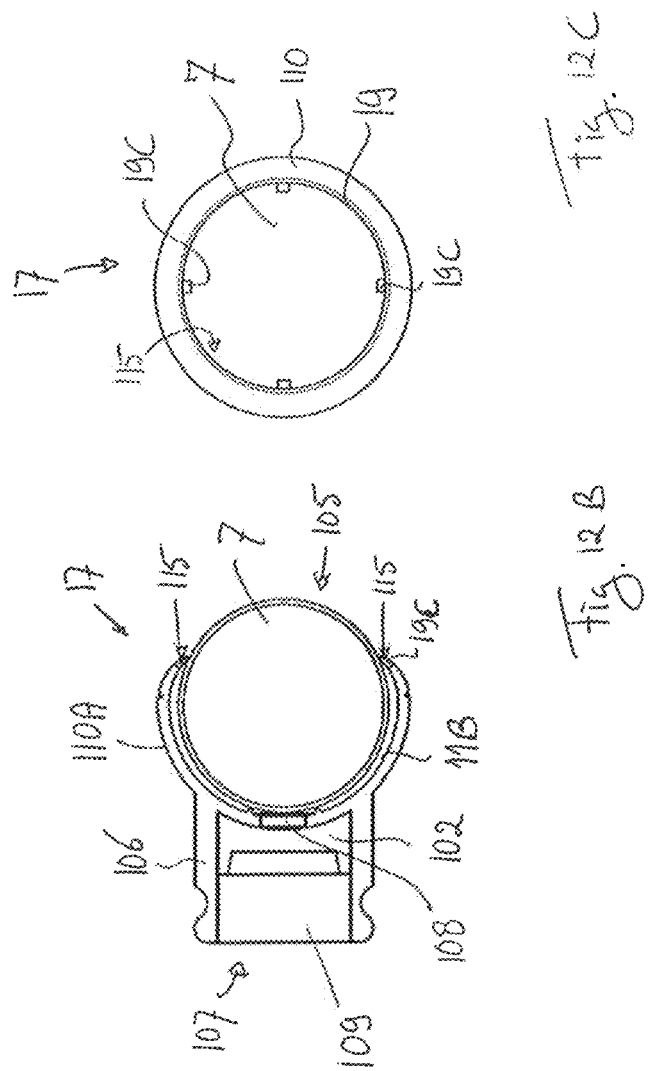

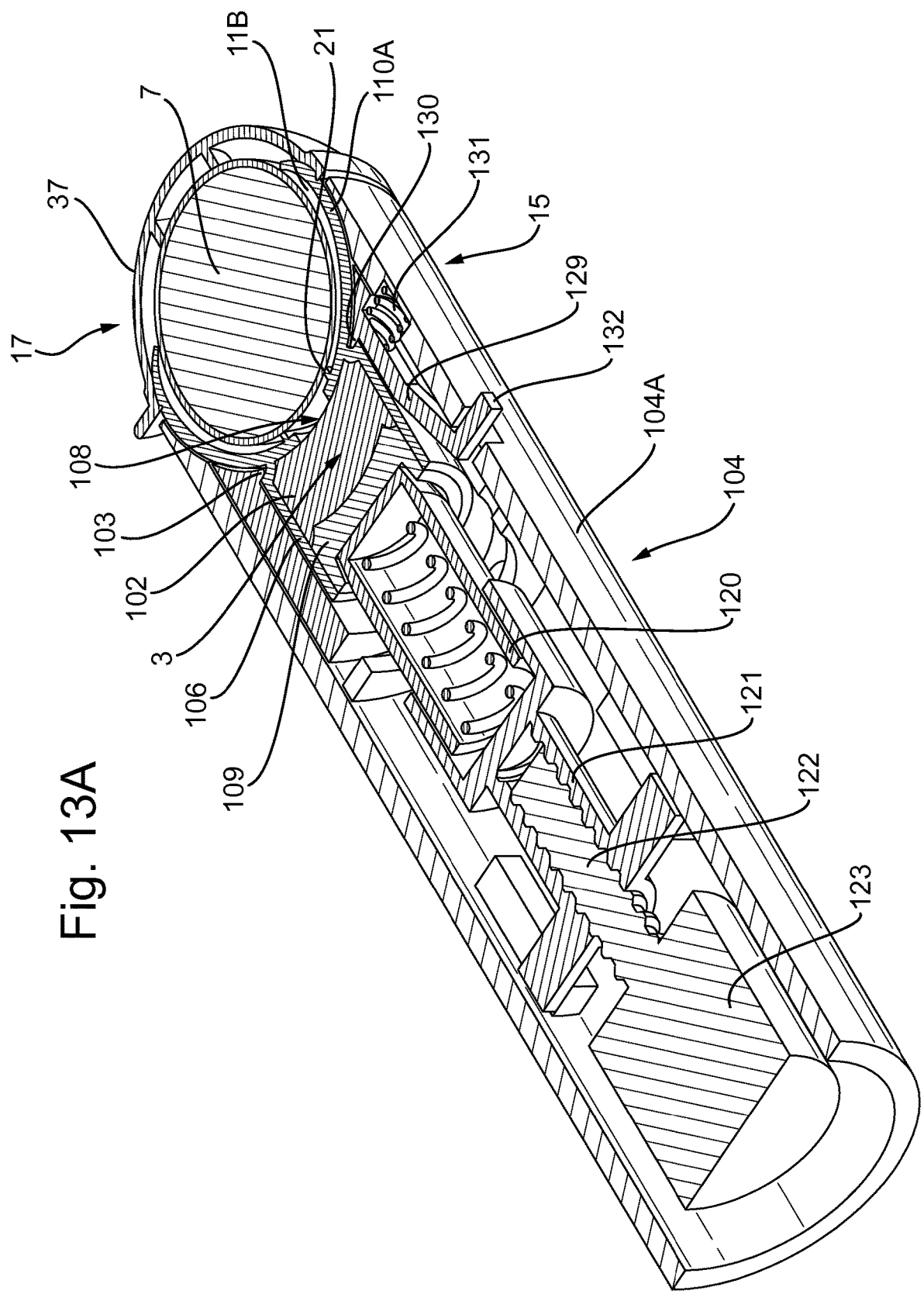

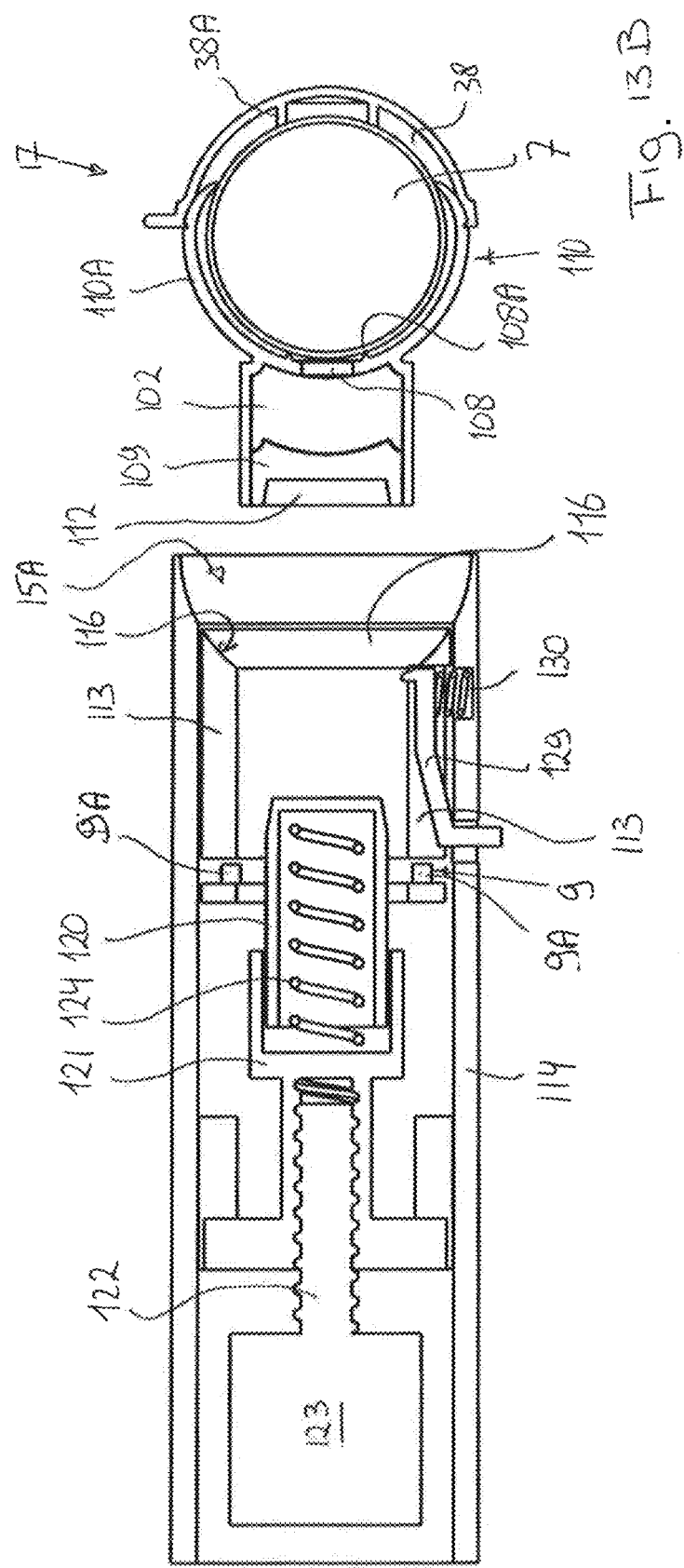

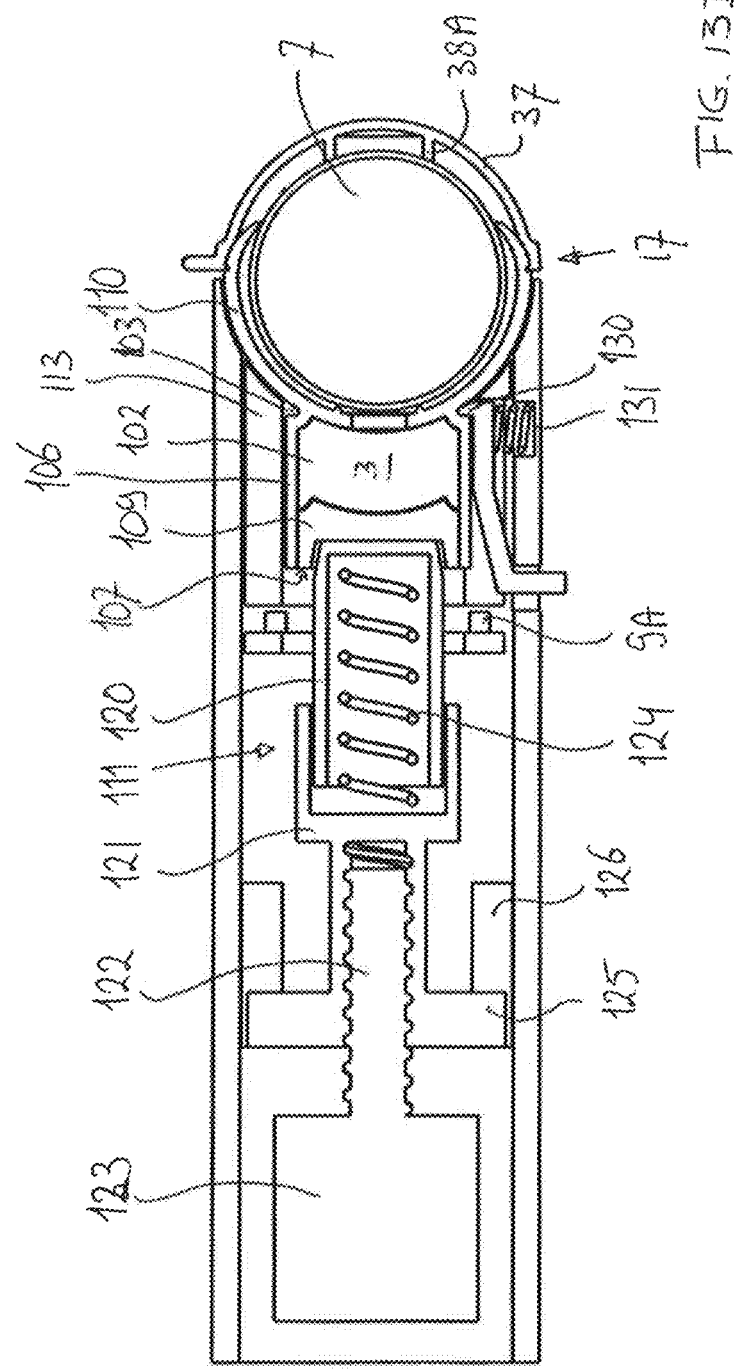

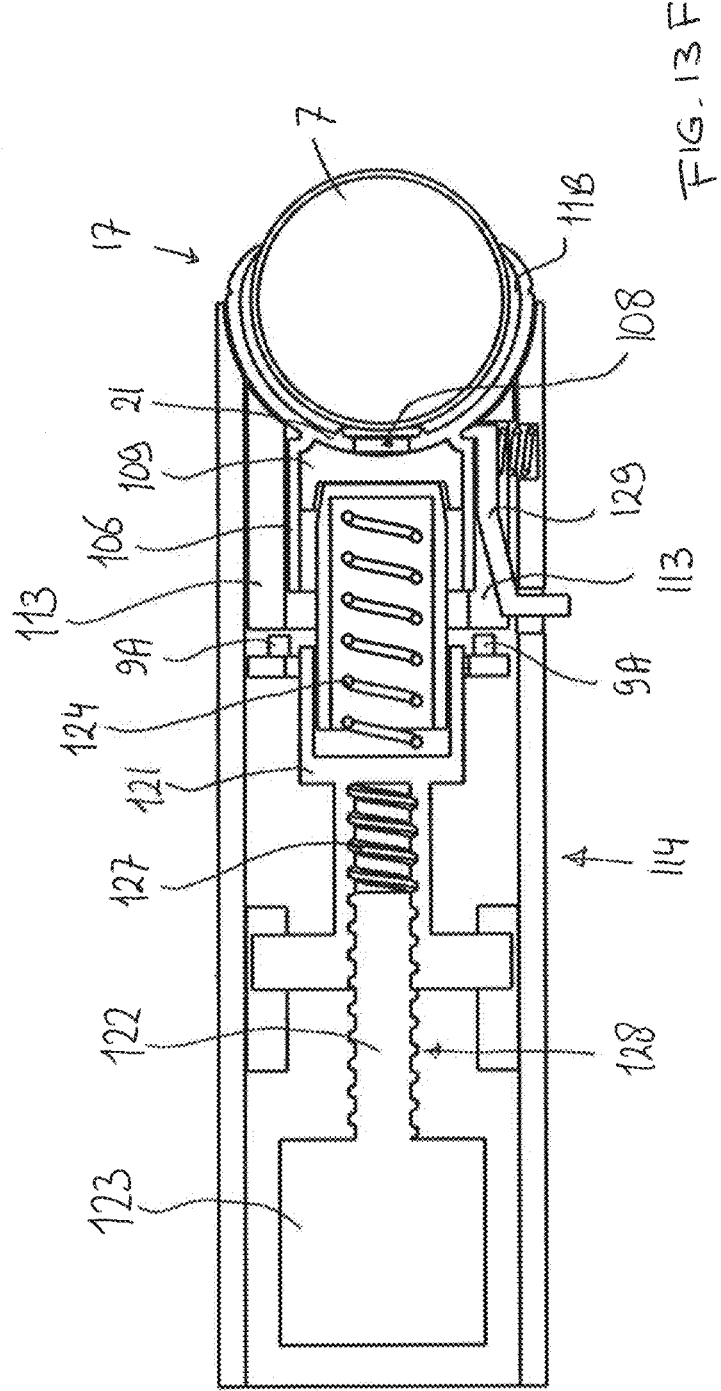

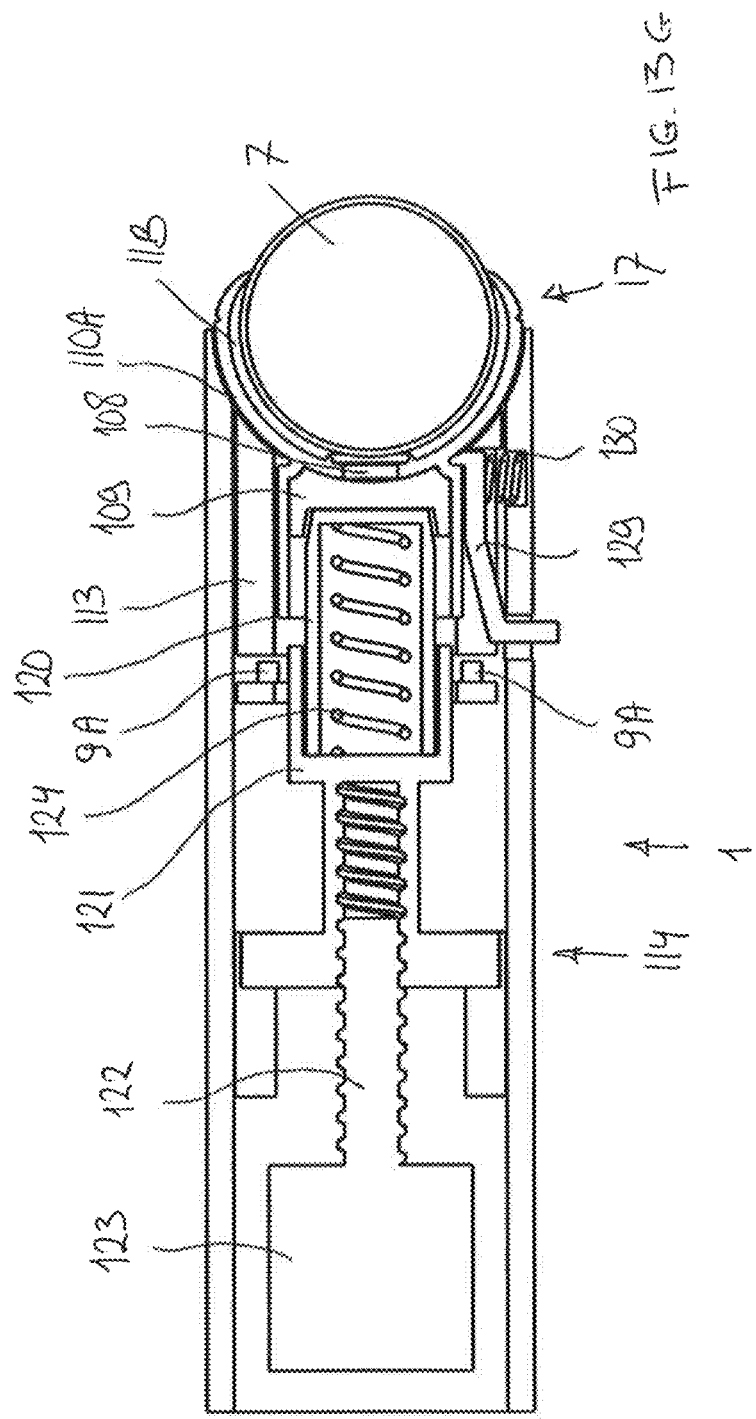

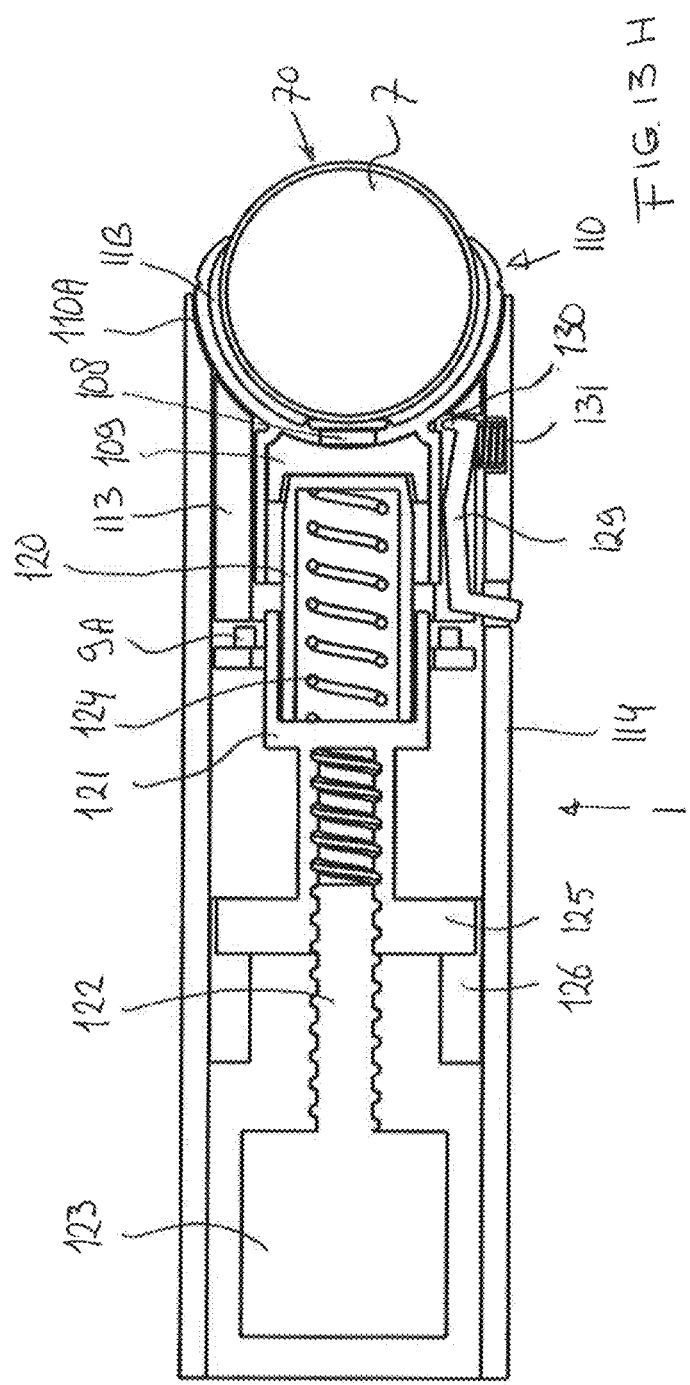

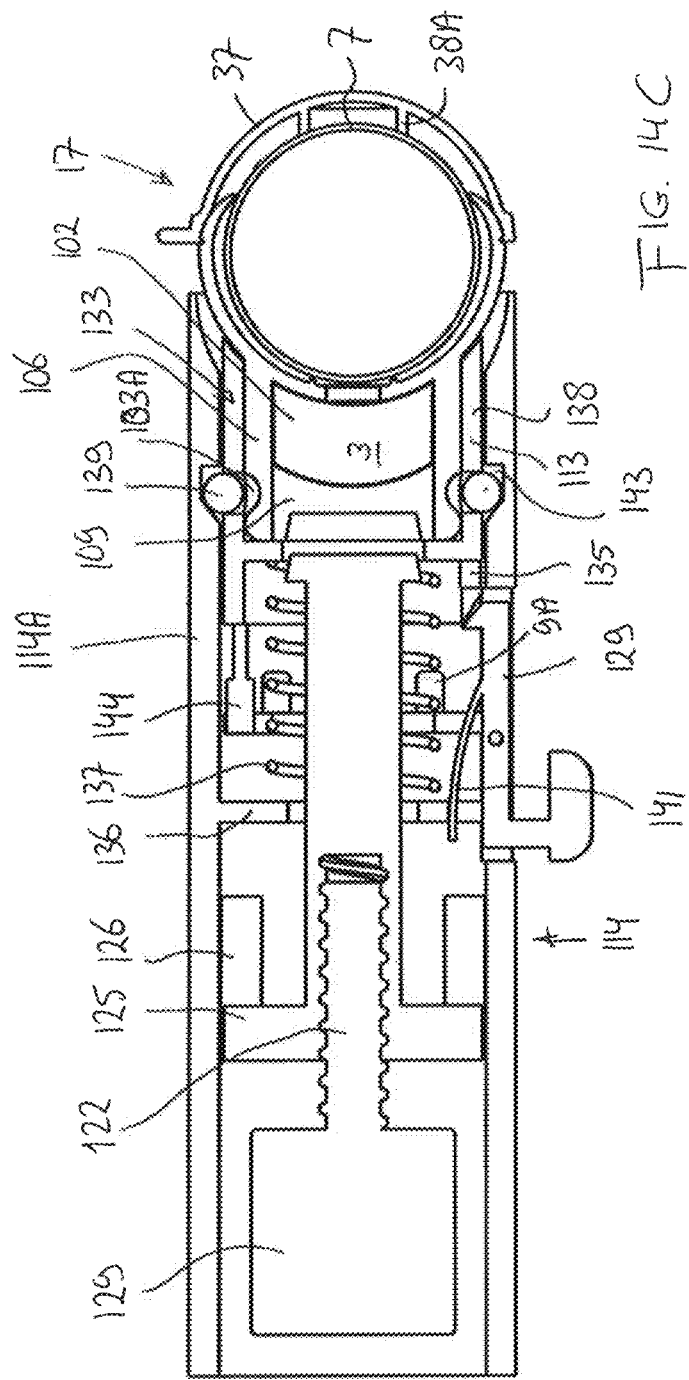

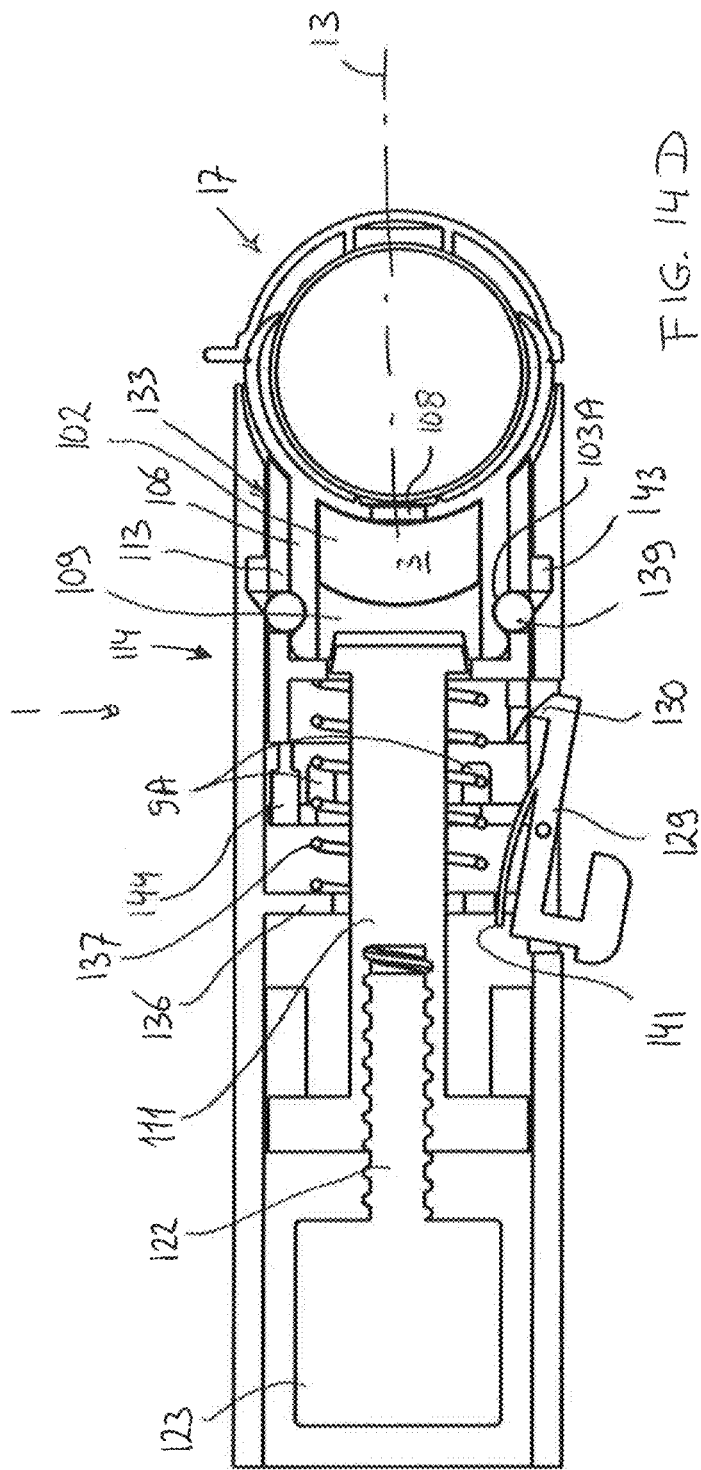

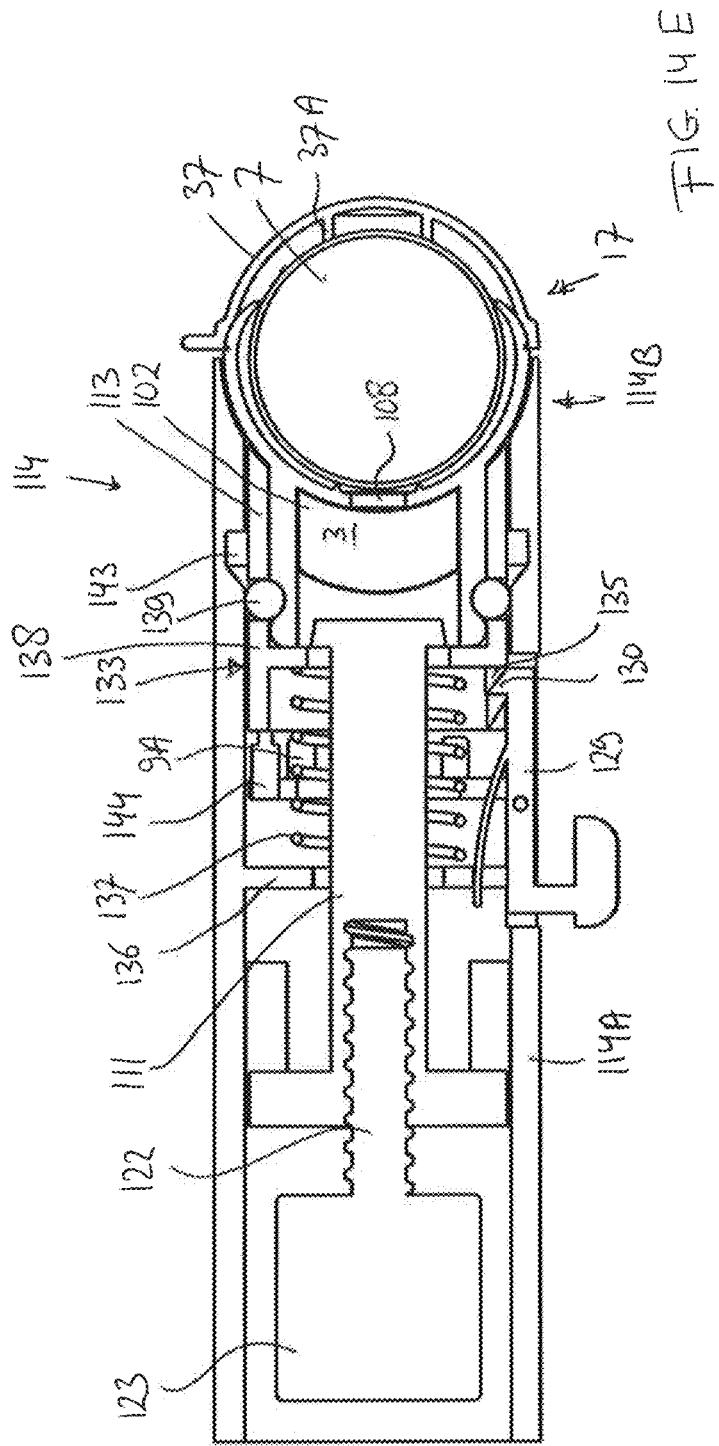

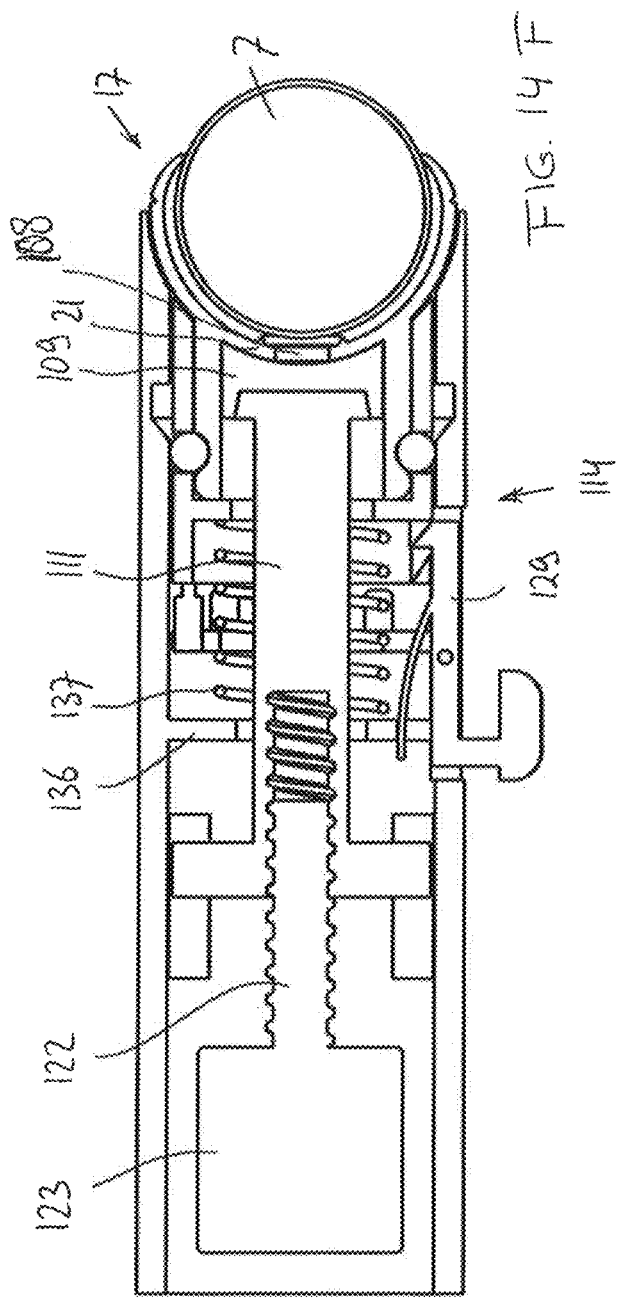

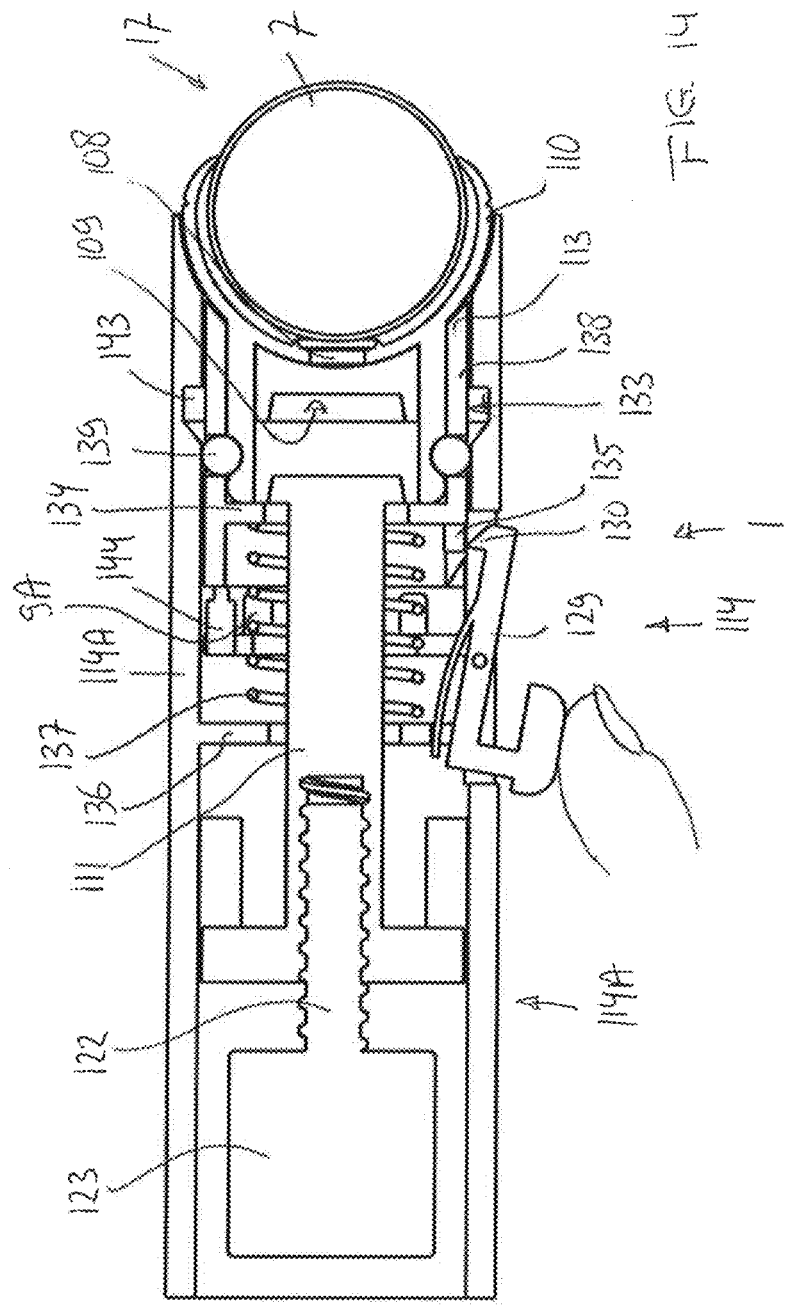

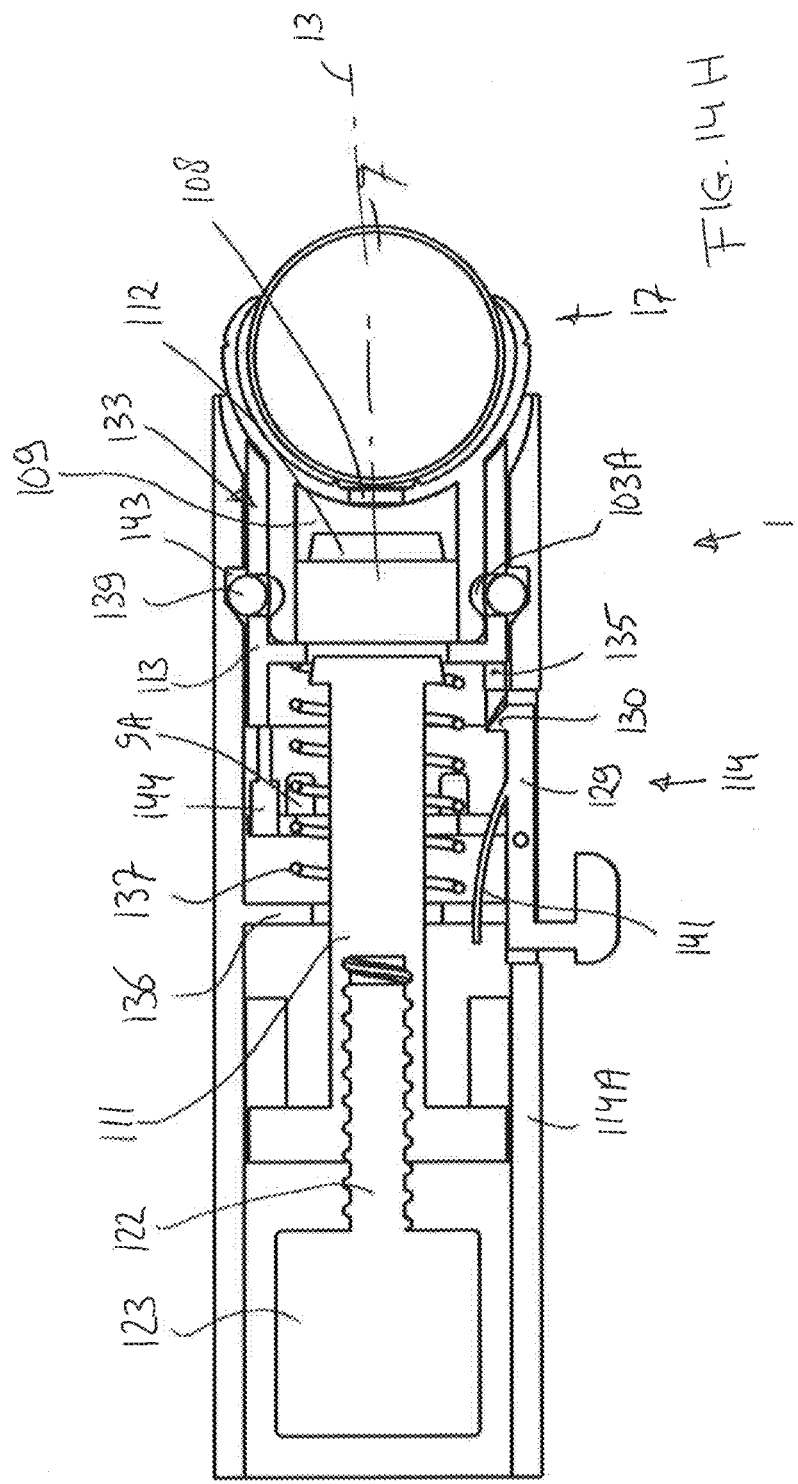

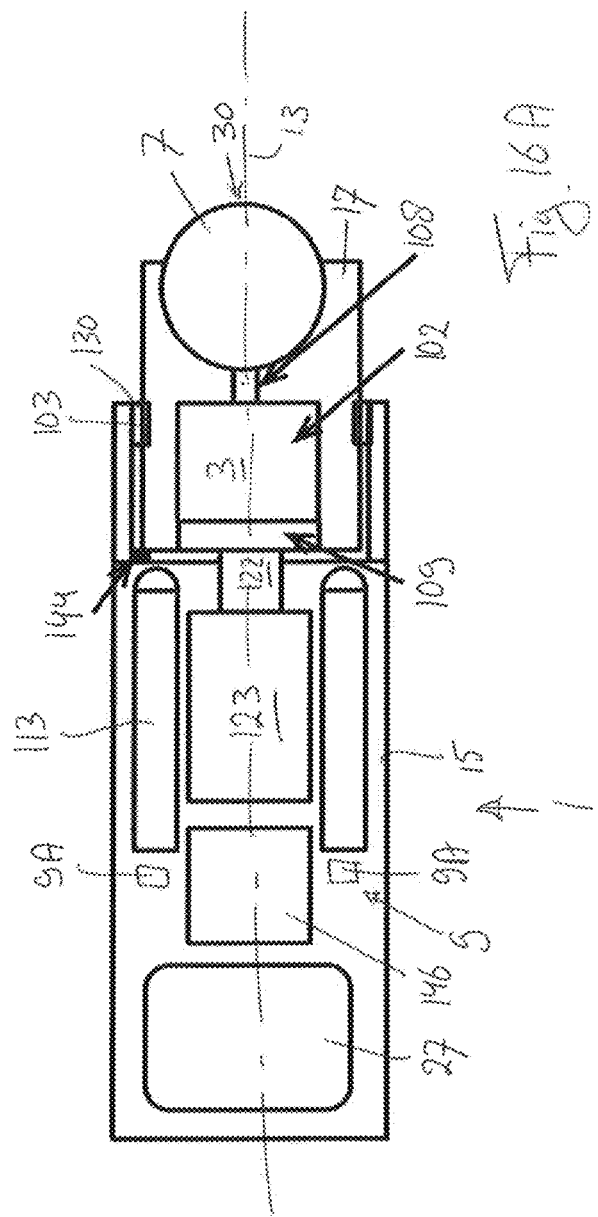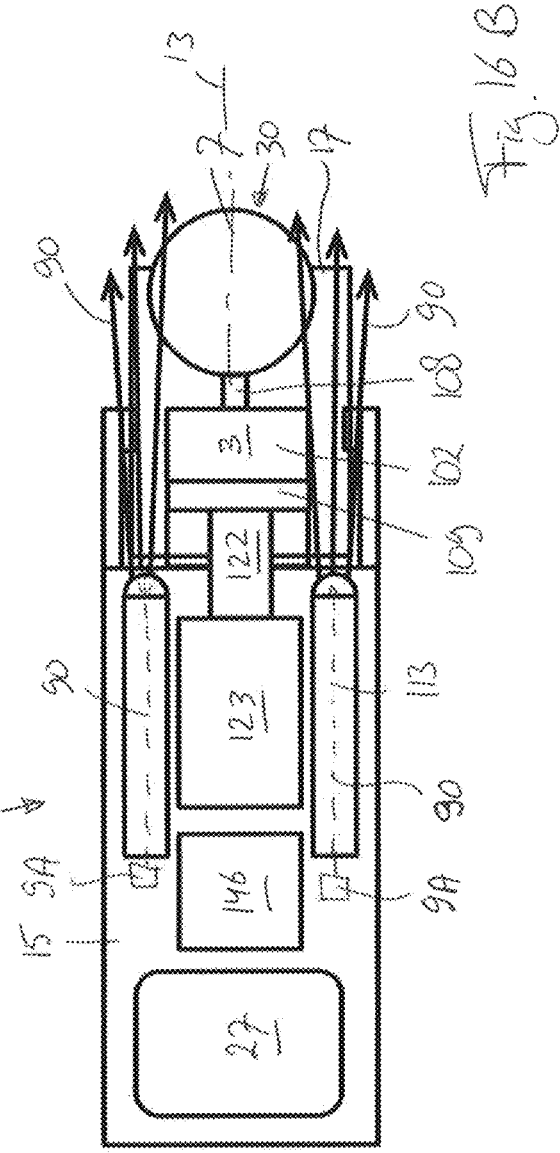

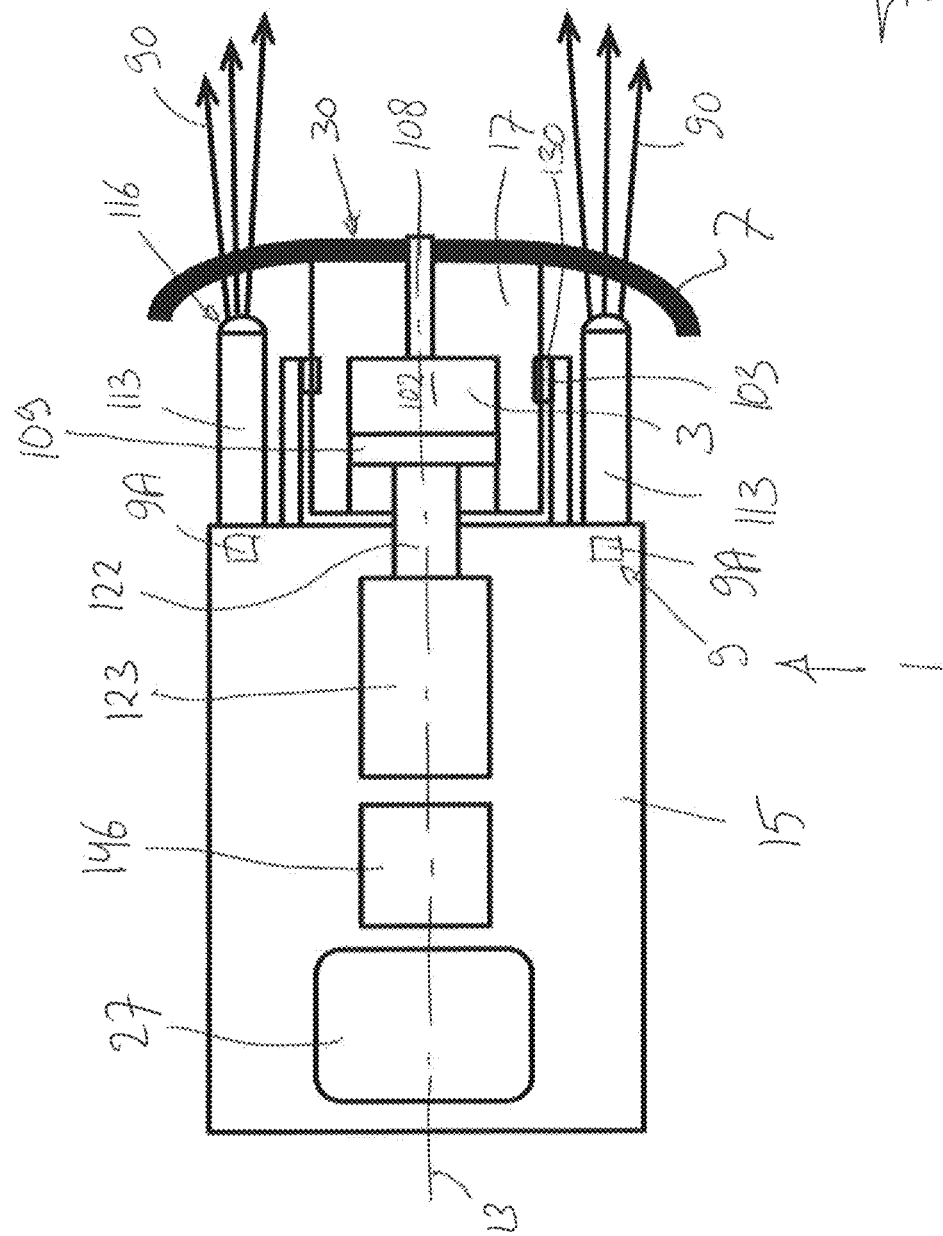

APPLICATOR AND CAPSULE FOR SUCH APPLICATOR

RELATED APPLICATION DATA

This application claims the benefit of U.S. provisional application Ser. No. 62/012,568 filed Jun. 16, 2014, hereby incorporated by reference herein in its entirety.

The invention relates to an applicator for applying a product and light to an application surface, especially the dermis or epidermis of a skin. The invention further relates to a capsule for applying at least a product to a surface, especially the epidermis of a skin.

For dispensing a product to a surface, such as a substance to a epidermis of a skin, it is known to use dispensers with an applicator element such as a ball which can be rolled over said surface. The substance is taken up by the ball from a reservoir in the applicator and transferred to the surface over which the ball is rolled.

Moreover it is known to apply light to a surface, for example for optimizing effects of a substance applied to said surface.

From US2008/262394 an applicator is known for dispensing a light to human skin, which applicator is a hand piece comprising a rolling ball as a massaging element and a connector for connecting the hand piece to a light source in a control device. Light from said light source is passed to the hand piece though a light connection such as an optical fiber and then radiated through or alongside the ball onto the surface to be illuminated. The ball is held in the hand piece in a ball chamber. In one embodiment the hand piece is provided with a plurality of openings around the ball, or a gap around the ball, through which cooling/warming air/liquid or massage oil/lubricant may be delivered to the skin during treatment of the skin. In US2008/262394 such liquid to be dispensed is, during use, injected into the ball chamber through a tube connected to the hand piece, from a source outside the hand piece.

From DE3905517 a hand held device is known comprising a rolling ball in a ball chamber, surrounded by a reservoir containing a fluid to be dispensed. The fluid can be picked up by the ball when rolling and be dispensed onto the skin. Light can be radiated onto and through the ball for heating the ball and for light therapy.

US2011/0106067 discloses an applicator device for applying a substance to skin, comprising a handle and a head. The head comprises a permanent part for connecting to the handle and a disposable part comprising a base, a volume of a substance to be dispensed and a sponge for dispensing the substance. The sponge is semi spherical and is molded to the base, such that between the base and the sponge a volume for the substance to be dispensed is provided. The outer semi spherical surface of the sponge provides for an application surface and the sponge is perforated for allowing the substance to be transmitted through the perforations onto the users skin. The handle is arranged to create a rotating magnetic force by rotating a first magnet by a motor or via electromagnetic field induction. A transmission is provided in the permanent part of the head for transmitting power from the handle to the head. A second magnet is provided in the head, within a ring-shaped stator. The second magnet is rotated by the rotating magnetic field and is used as an energy source in the head. The disposable part of the head is arranged to release a portion of the substance from the volume through the perforations of the sponge dependable upon the power transmitted from the permanent part of the head. In this device the sponge will be deformed during delivery of the product onto skin, and will absorb at least part of the product. Moreover, the sponge bounds the reservoir and thus the dispensing of the product will at least in part be controlled by the forces applied onto the sponge.

In an embodiment the disposable part comprises a central opening. The permanent part of the head comprises a tubular extension which at a free end is provided with four LED's. When the disposable part of the head is mounted on the permanent part, the tubular extension will fit in the central opening, such that the LED's extend outward from the semi spherical surface of the sponge.

US2011/0040235 discloses transdermal delivery device for therapeutic agents which comprises fixed in a housing a mechanical vibration element, a light source and a heating and cooling element. An end of the housing forms an application surface. In some embodiments a reservoir containing a therapeutic agent may be comprised in the housing, spaced well apart from the application surface, connected thereto by a series of narrow conduits. In one embodiment the reservoir is provided as a replaceable pouch with tangible closures for connecting to the conduits. A piston is provided with a piston rod extending through the end of the housing opposite the application surface, which can be engaged by a user for forcing the piston against the pouch, such that product is dispensed. Alternatively an embodiment is shown in which the reservoir is an integral part of the housing.

US2009/0299236 discloses a device for therapeutic light treatment, in which a ball is rolled over a skin surface during which light is radiated onto the skin.

US2008/0014011 discloses a cosmetics and/or drug dispensing device, having a head portion. In embodiments a ball is provided in the head portion, as an applicator element, and a light source emitting light through the top of the head portion and/or through the ball. In embodiments the entire device can be dispensable, in other embodiments a disposable cartridge comprising a cosmetic or drug compound can be mounted to the rear of the head portion. A similar device is disclosed in US2012/0207532, again disclosing a disposable reservoir containing a large quantity of product being mounted to a rear of a reusable head portion comprising a ball as an applicator element. The product is fed to the applicator element by natural flow, for example by gravity.

WO2010/111997 discloses an applicator device for cosmetic and/or medical use, having a ball as an applicator element. The device comprises a disposable applicator part and a reusable base comprising a power source and a vibrating element. In a semi spherical reservoir extending around the ball a substance is provided to be dispensed. Moreover in the applicator part compounds are contained, between the reservoir and the base, which need to be mixed for providing heating or cooling of the substance. A light source may be provided in the base, radiating light through the compounds, the reservoir with the substance and the ball, to be radiated on the skin. This means that during use the light will be influenced by these elements and the changes therein, such as the level and type of filling, temperature of the mixing compounds, air gaps between components and the like, which will make the system inaccurate. Moreover in WO2010/111997 the substance to be dispensed is apparently brought onto the ball by adherence between the ball and the substance.

An aim of the present disclosure is to provide an alternative system for dispensing a product and light onto a surface, such as onto the dermis of human skin. An aim of the present disclosure is to provide a capsule for dispensing a product onto a surface. An aim of the present disclosure is to provide an applicator system which can be hand-held, comprising a light source and a reservoir for fluid to be dispensed by means of an applicator element such as a ball, with which small volumes of product can be dispensed, preferably in a well-controlled manner. An aim of the present disclosure is to provide for a method and system for treating a surface, such as the dermis of skin, by applying a product and light onto said surface by an applicator element, with which a predetermined amount of product per period of time is dispensed onto said surface. An aim of the present disclosure is to provide an applicator system for applying a product and light onto a surface, such as human skin, in a hygienic and comfortable manner. An aim of the present disclosure is to provide for such applicator system in which during use the contact between the applicator and the skin of a user onto which a substance is applied is limited to contact between a disposable part and the skin. Preferably such applicator can be used in any position of the applicator in contact with the skin, even in vertical position.

At least one of these and/or other aims of the disclosure can be obtained with a system, applicator, capsule and/or method as disclosed in this disclosure.

In an aspect a capsule can be provided for distributing, on a surface of a living body, a product containing an active component or forming a cosmetic product, the capsule having a product distribution zone and comprising in a body, a supply of product which is in communication with the product distribution zone, and first linking means for removably securing the capsule to second linking means of a housing in which is disposed a light source.

In an aspect a product distribution device can be provided containing an active component for distribution on a surface of a living body and the radiation towards this surface, the device comprising a distribution capsule and a housing to which the capsule is secured in a removable manner, by first and second linking means, and in which is disposed the light source adapted for emitting said light ray(s) towards the product distribution zone.

In a further aspect a device can be provided for distributing, on a surface of a living body, a product containing an active component or forming a cosmetic product, and the release/discharge, at least as far as this surface, of energy in the form of (a) light wave(s), the device comprising a distribution zone of product on said surface and at least one light source emitting at least one light ray towards the surface, for example focused or, preferably, spread out over a wider zone, for example over a contact zone between a movable element and the skin.

In a still further aspect a capsule, can be provided, for example for use with a device as described here above, wherein the capsule comprises a ball rotatably mounted in a housing, wherein the housing comprises a reservoir having a movable and/or deformable wall, for containing product to be dispensed by the ball, and wherein the reservoir is in communication with a space between the ball and the housing through at least one opening. The opening is preferably relatively small. The reservoir preferably has a volume for a relatively small amount of product.

According to the present disclosure a capsule preferably is disposable and preferably comprises a relatively small amount of product to be dispensed, such as for example an amount sufficient for a single application cycle, which can for example comprises a series of dispense steps.

In a still further aspect a method can be provided for applying product and light to a surface, wherein a capsule comprising a reservoir containing product is releasably coupled to a housing comprising at least a light source and a control unit. The capsule comprises a movable element such as a ball onto which product from the reservoir can be fed for dispensing it to a surface by the ball, wherein light is transmitted from the light source through the capsule to the said surface prior to, during and/or after dispensing said product onto said surface, whereafter the capsule is removed from the housing and replaced by another capsule. The capsule comprises preferably a relatively small amount of product.

Other characteristics and advantages connected to the suggested solutions will become clear from the following detailed description of various embodiments where reference numerals refer to the annexed drawings provided by way of example and where:

FIG. 1 is an example of an applicator device of a product of which the interior is shown, according to a longitudinal central section, FIG. 2 is also a longitudinal central section, but only of the capsule containing the supply of product and the movable element.

FIG. 3 is a view according to FIG. 1, moreover partial and schematic, of the emission of the light radiation, FIGS. 4 and 5 shows safety means defining an interrupter which allows the emission of the light radiation to only intervene if it is axially supported and closes the electric circuit where the light source is situated; in FIG. 4 the circuit is open, in FIG. 5 the circuit is closed, FIG. 6 shows a joint action of the product/radiation on the skin, with a focal regulated on the level of the dermis, FIG. 7 is a central longitudinal section of a variant of the device FIG. 8 is a view of the only deep deformable piece 49 of FIG. 7, the arrows indicating the deformations.

FIG. 12A shows in cross section schematically part of a applicator unit and a capsule, for a general discussion of active dispensing;

Figure 13C:
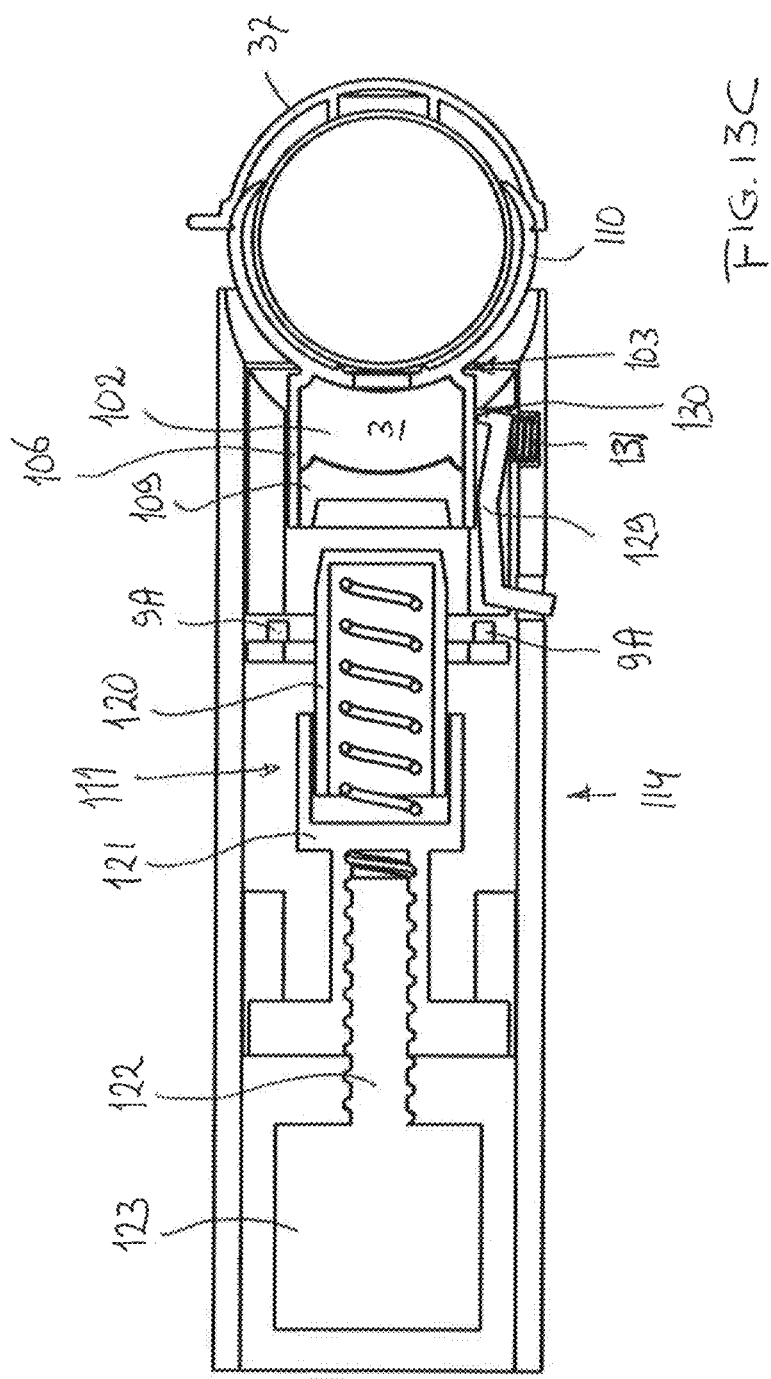
Figure 13E:
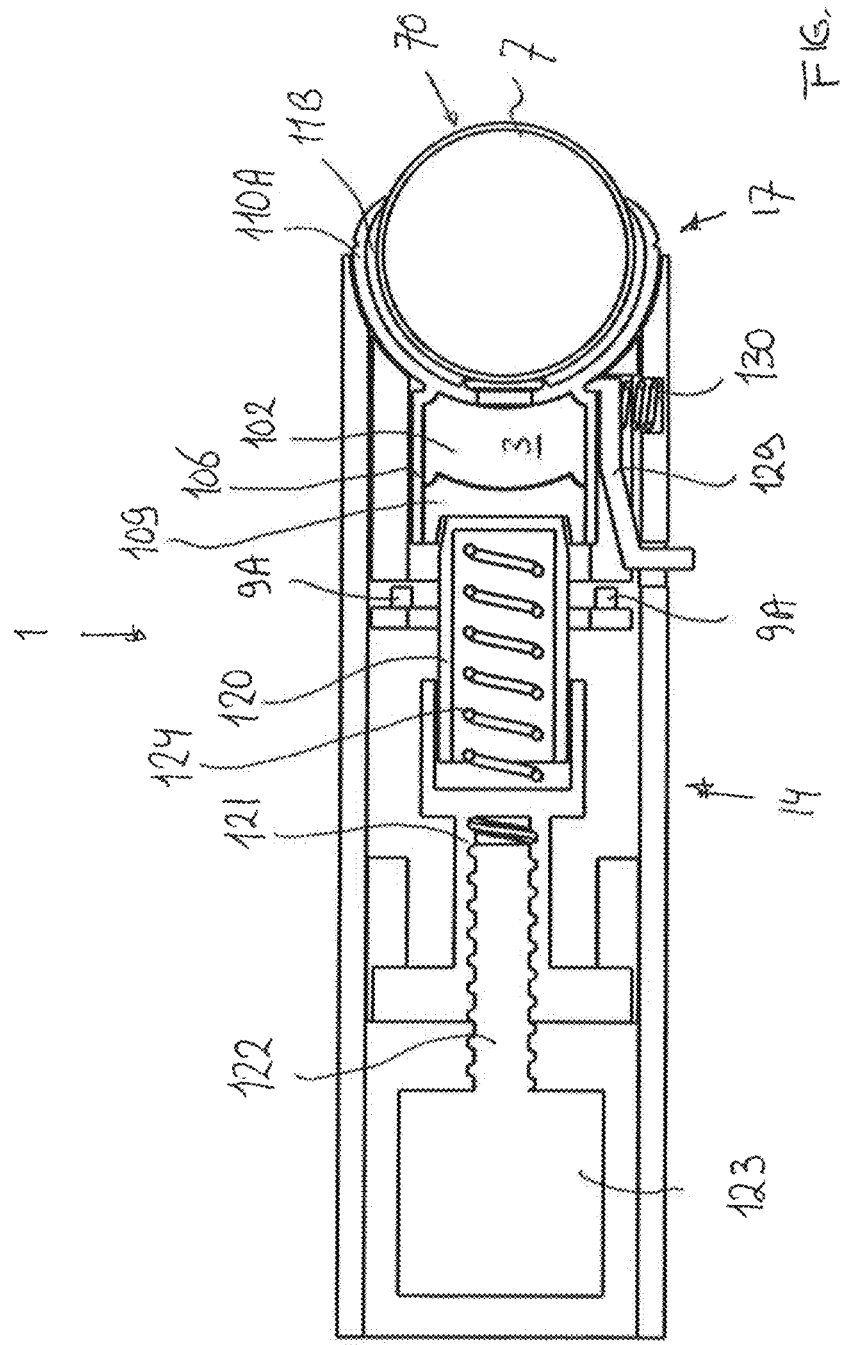
Figure 13I:
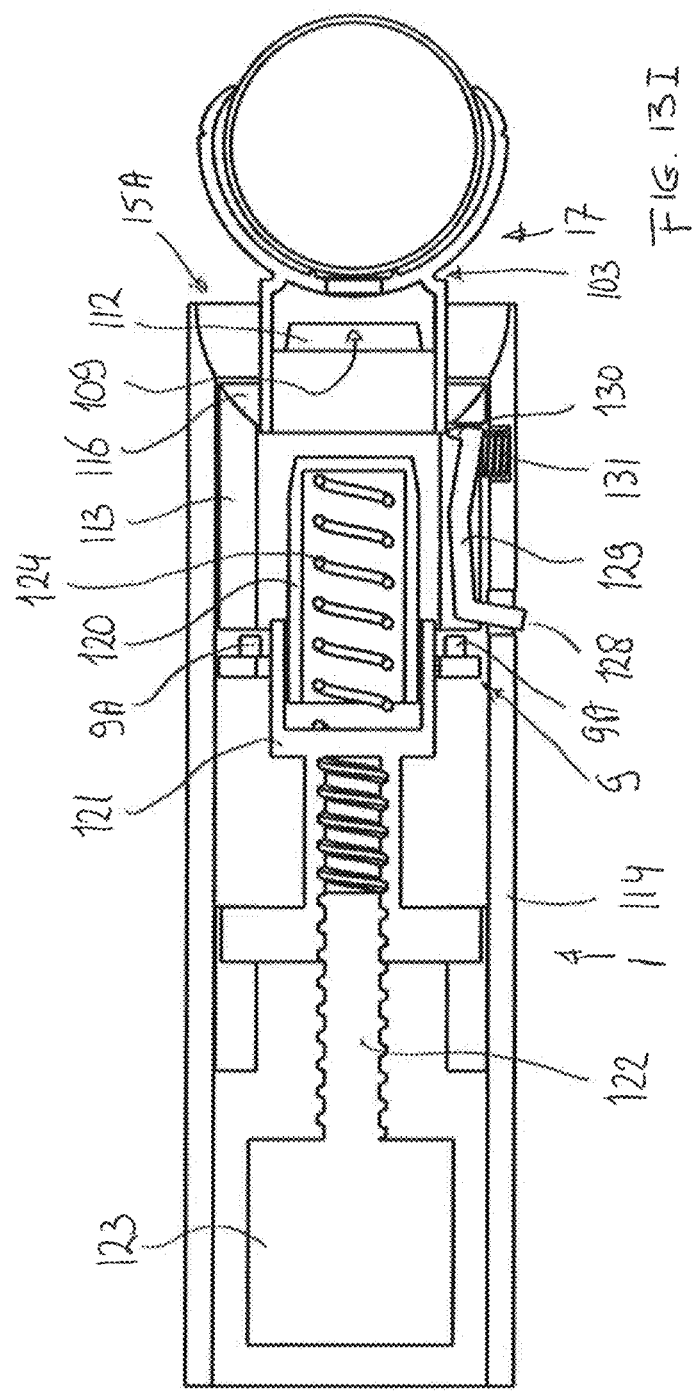
Figure 14A:
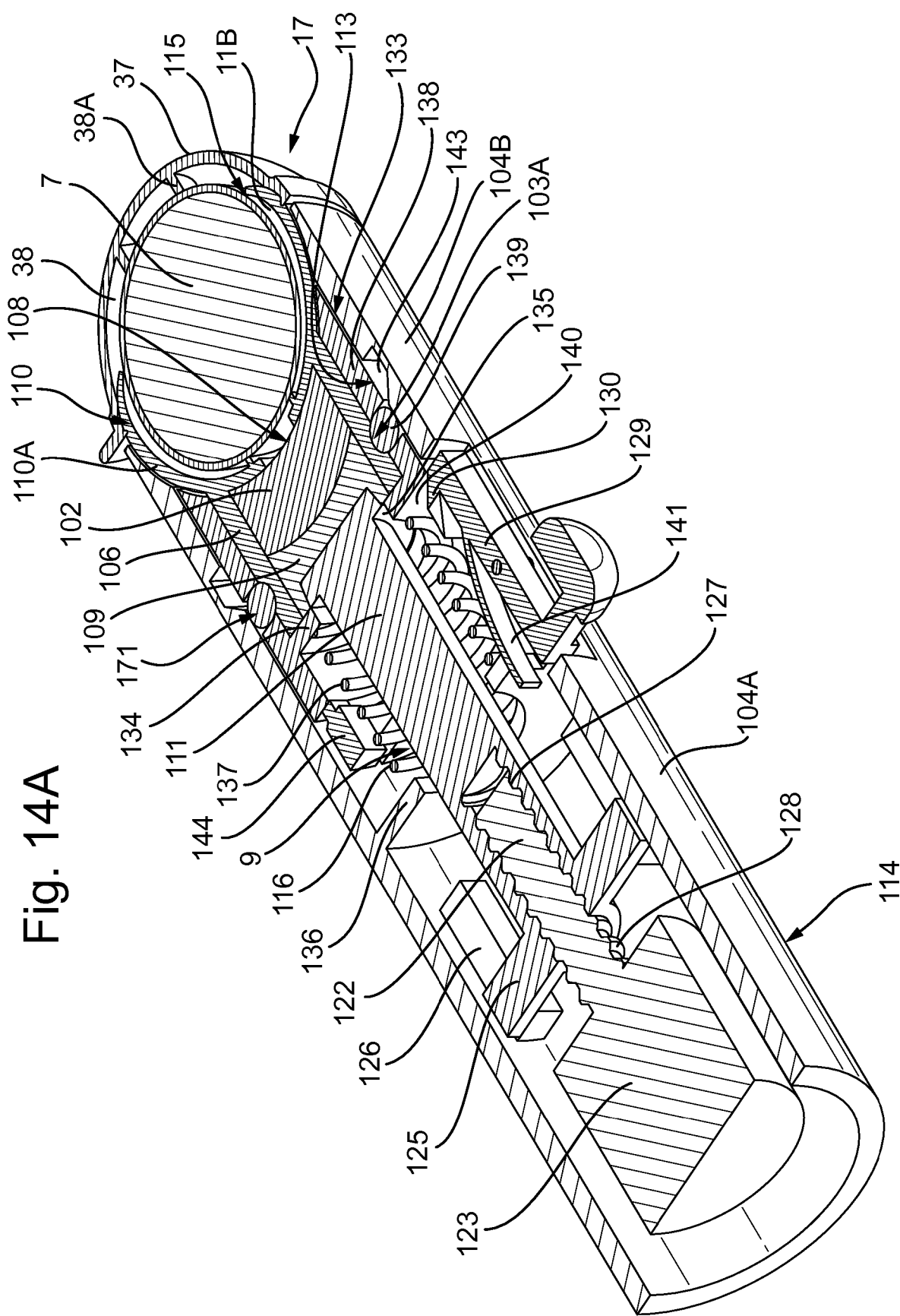
Figure 14B:
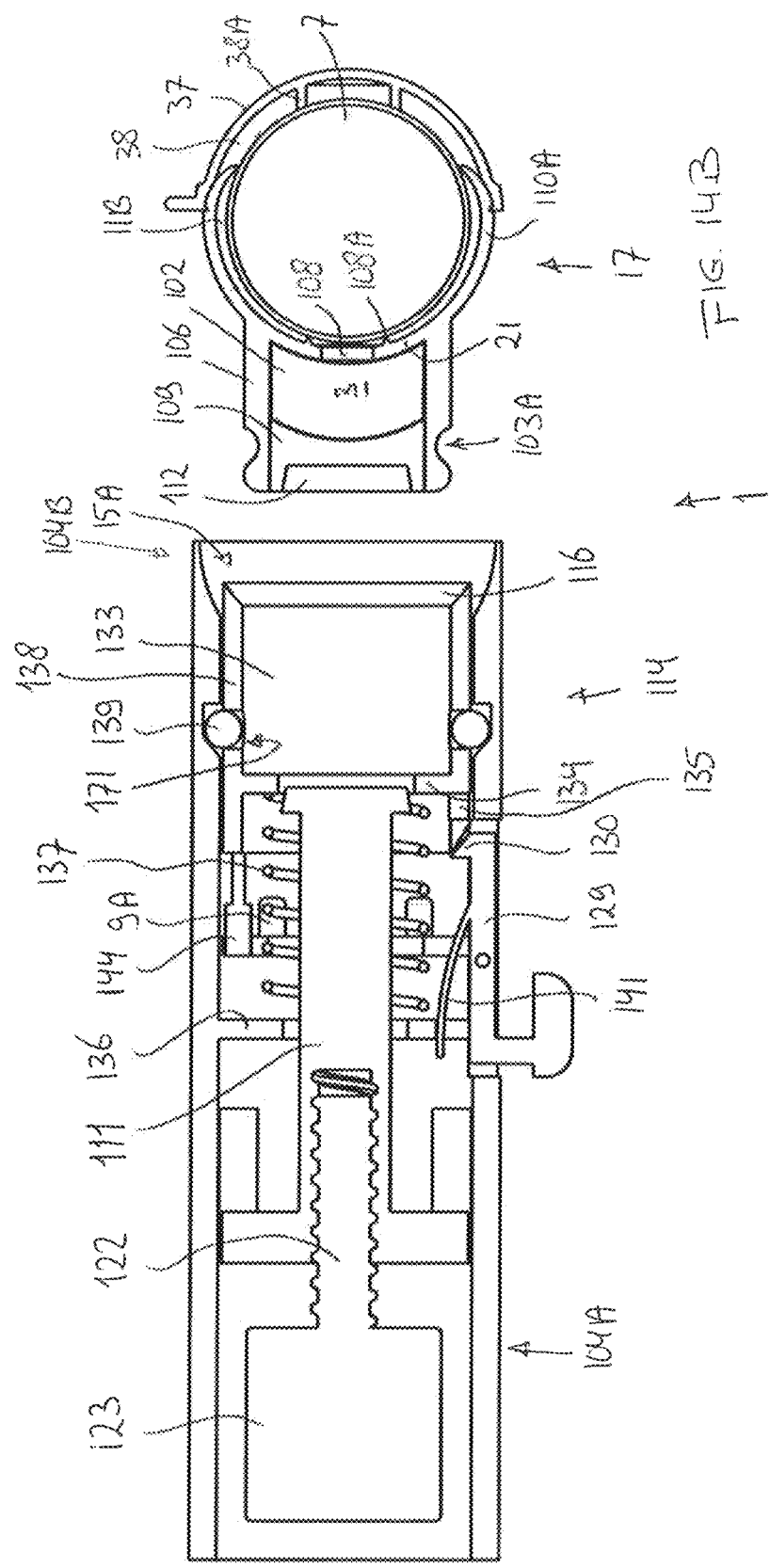
Figure 14:
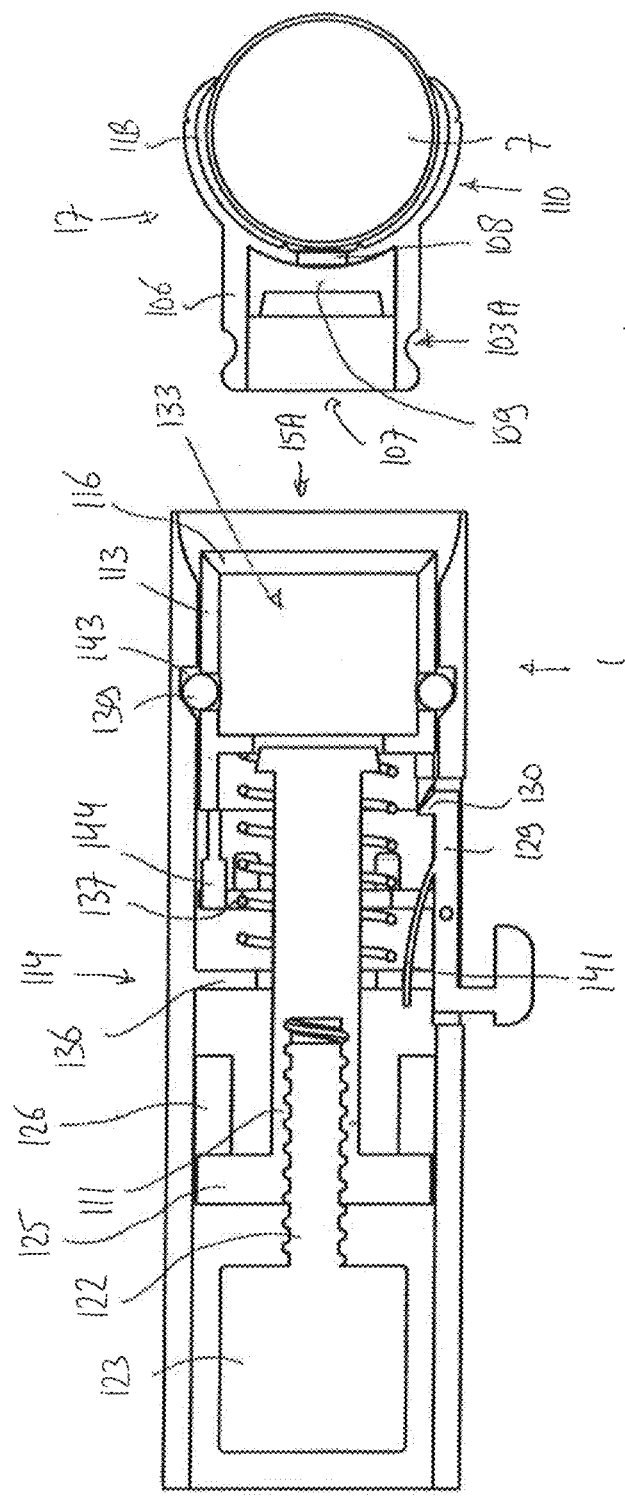
Figure 15A:
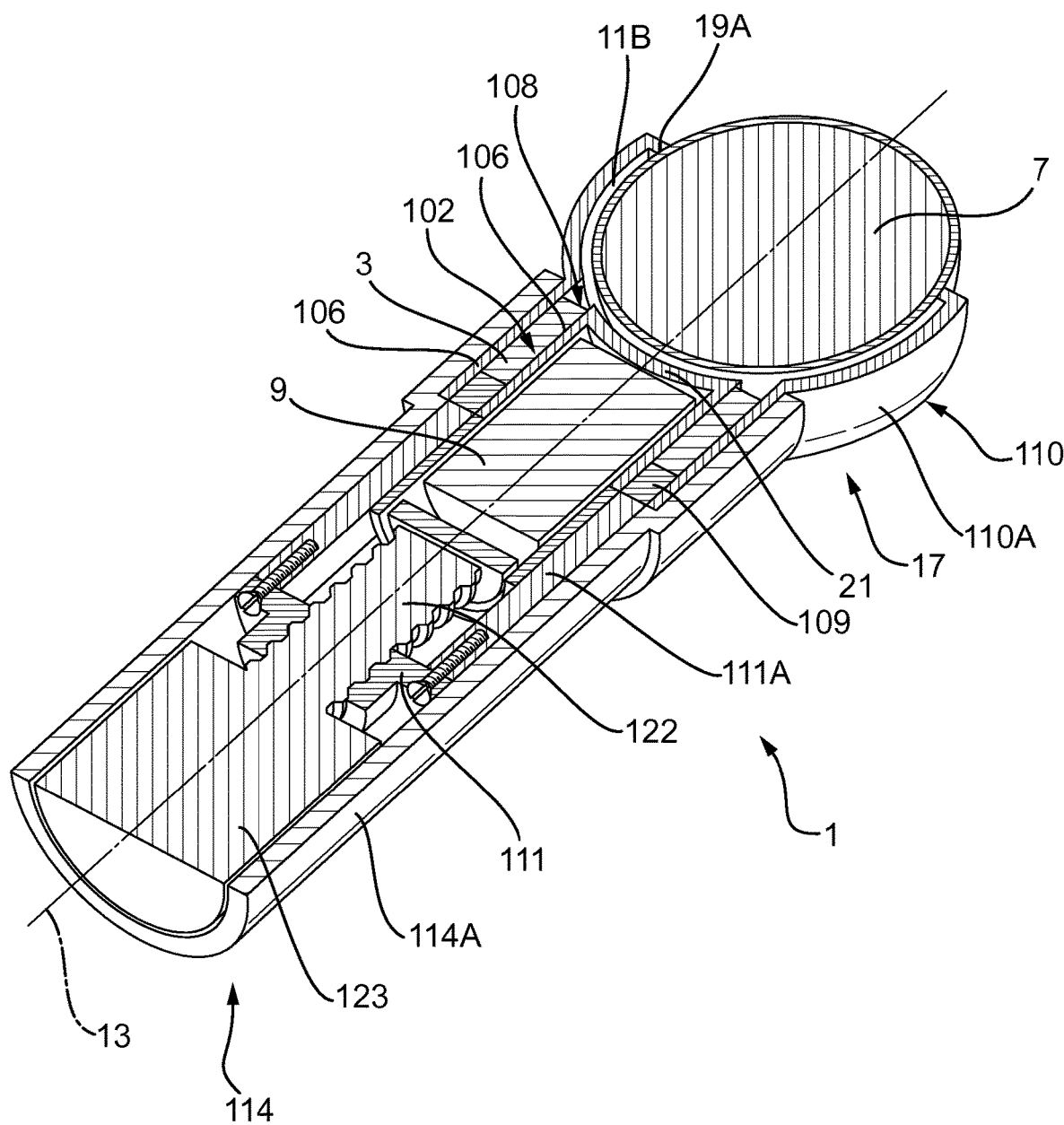
Figure 15B:
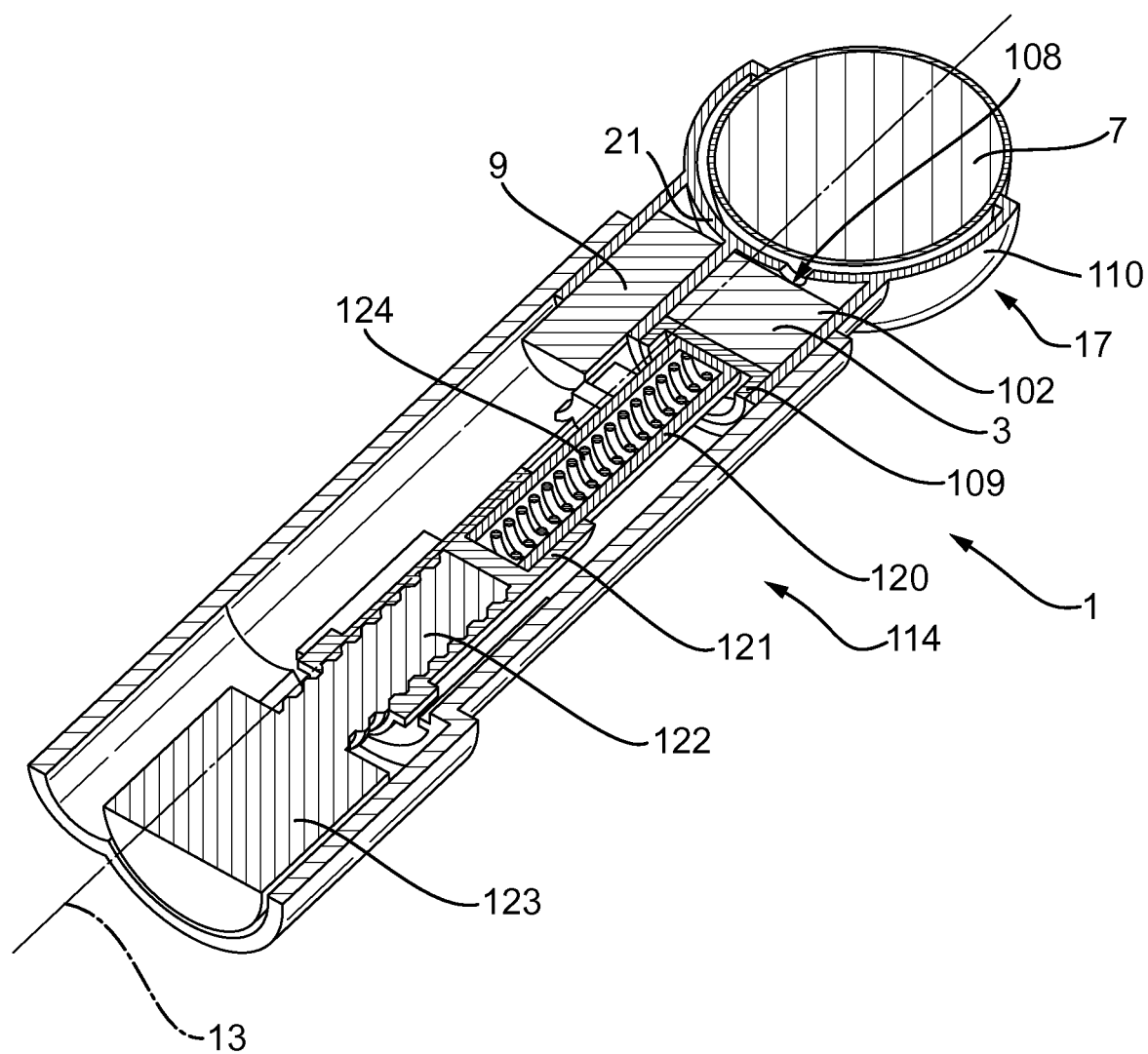
Figure 15C:
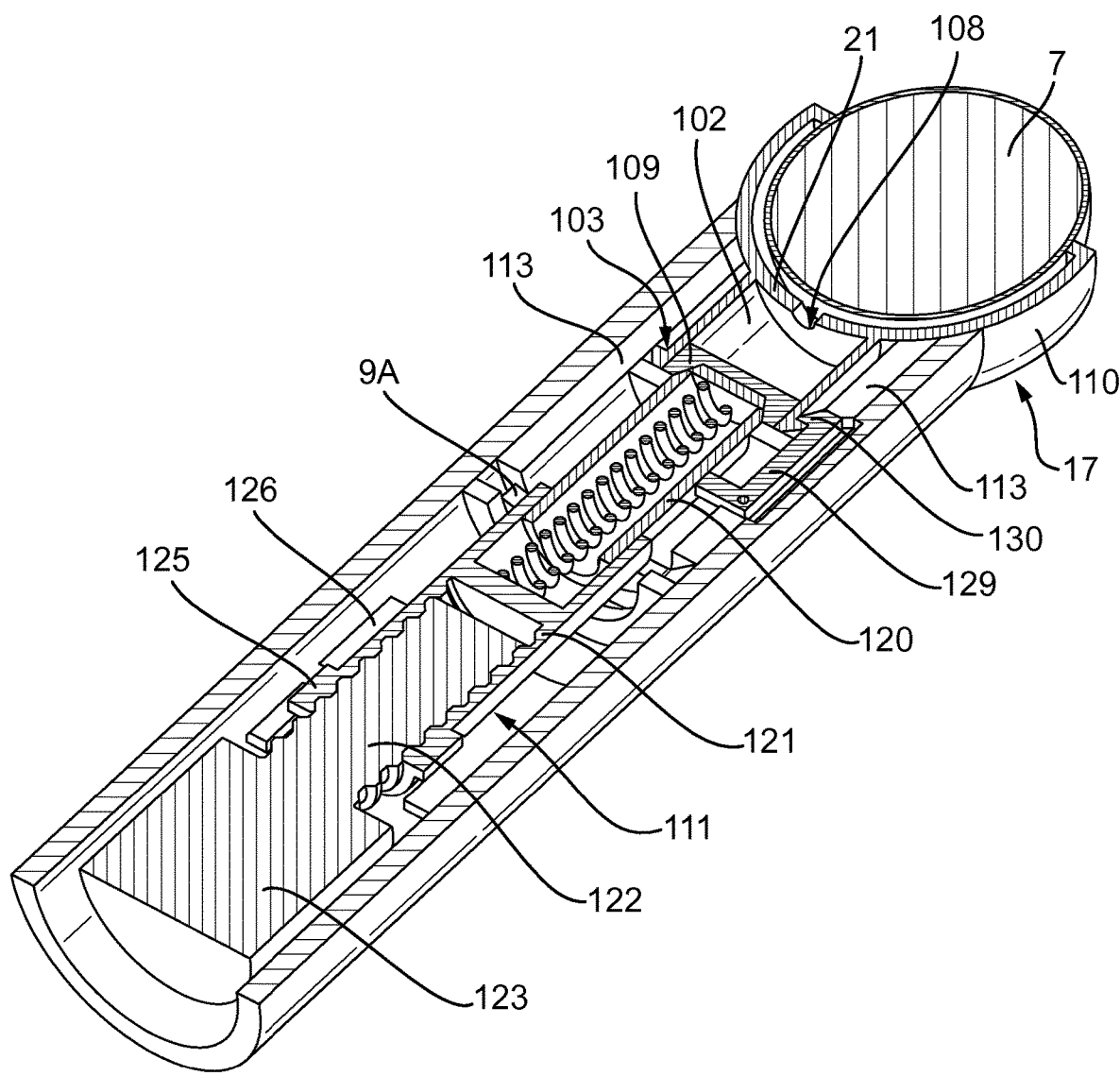

FIGS. 12B and C shows schematically a ball in an embodiment of a capsule housing, in cross sectional side view and frontal view;

FIG. 13A-I shows schematically a first embodiment of an assembly for active dispensing;

FIG. 14A-I shows schematically a second embodiment of an assembly for active dispensing;

FIG. 15A-C show three alternative embodiments of units 114 for active dispensing, as discussed with reference to especially FIG. 12-14, wherein the same or similar elements and features have the same or similar reference signs.

FIGS. 16A and B schematically show in cross section a further embodiment of a device, in which at least part of the light emitted passes the applicator body formed by a ball;

FIG. 17 schematically shows a still further embodiment of a device having a non-movable applicator surface.

The present invention is by no means limited to the embodiments disclosed and discussed specifically in this description. Many alternative embodiments are considered to also have been disclosed or covered by the claims, including but not limited to combinations of embodiments or parts thereof as disclosed herein, including but not limited to embodiments and parts and features thereof as shown in and discussed with reference to the drawings.

In embodiments for example more than one reservoir could be provided, opening into the space around the movable element, such that components or products can be dispensed which will be mixed only upon application, for example components which would not provide a stable product over a longer period of time or which provide a chemical or physical reaction upon mixing which is desired to happen at or near said surface 5. The reservoir for active dispensing could be designed differently, for example as a flexible pouch, compressible by the push rod or by for example squeezing it. To this end for example the pouch could be pressurized by gas pressure or mechanically. Alternatively the reservoir could have a membrane or otherwise deformable wall in stead of the piston, which could be deformed by the push rod or in a different manner, for dispensing the product. A capsule could be provided with a light source, in stead of or additional to that in the holder 15. Multiple movable elements could be provided in a capsule, for example two or three such elements such as balls or rolls. A device according to the disclosure could be provided with an indicator system such as an alarm, for example by light, vibration and/or sound, indicating to a user that the applicator element should be moved to a next surface or part of a surface for dispensing a next amount of product in a next step. In embodiments the entire device could be disposable or reusable. However, disposable capsules 17 used with a reusable holder 15 are preferred.

These and other variations are considered to have been disclosed herein as well.

In this description embodiments of an applicator, capsule and method for dispensing are disclosed by way of examples only. In the different embodiments the same or similar parts and features have the same or similar reference signs. The products to be dispensed as discussed can be used in all embodiments, unless specifically discussed otherwise.

In this description wording like substantially or about should be understood as meaning that a value or property it refers to does not have to be met entirely. Small variations can be possible, such as for example 20% or less of the given value, for example less than 15%, such as for example 10% or less, or at least 5% or less.

In the present disclosure an applicator, also referred to as device 1 is to be understood as at least meaning a device comprising a housing which houses at least a light source and an energy source or connector for such energy source and a capsule releasably connected to or connectable to said housing, an applicator element and a reservoir for a product to be dispensed. Preferably the capsule comprises the applicator element and the reservoir.

In the present disclosure a capsule can be understood as meaning at least an element to be connected to or connectable to a housing as described, which capsule comprises at least first coupling or linking means or elements, for cooperation with second coupling or linking means or elements provided in and/or on the housing.

A capsule according to this description preferably is disposable, which can be understood at least as meaning that it contains a relatively small amount of product, especially an amount of product for a single treatment procedure, is made of relatively inexpensive materials and can be discarded after dispensing at least most of said small amount of product and/or after said single treatment procedure.

By using such disposable capsule, which could also be referred to as cartridge or pod, different advantages can be obtained. By using a new capsule for each treatment procedure it can be guaranteed that the right amount of product is dispensed during such procedure, or at least no more than a desired maximum. Moreover hygiene can be more easily guaranteed since the same capsule and especially the same applicator element will not be used for different treatments or by or for different users and/or surfaces. It may for example be prevented that contaminations picked up by the applicator element will be carried into a reservoir of product to be dispensed in more than one treatment procedure. Moreover the element that would normally require the best cleaning after use can now be discarded, limiting the necessity of meticulous cleaning. Furthermore it will be easy to switch between products to be dispensed. A further advantage can be that the quality of product contained inside the reservoir of said capsule can be guaranteed better, especially when the product may be susceptible to for example deterioration by aging or oxidation.

In this description a relatively small amount of product contained in the reservoir can for example be less than 10 ml, more specifically less than 5 ml, more in particular less than 3 ml, such as for example between 0.01 and 1.5 ml.

During use the product may be dispensed from the reservoir in a continuous or semi continuous flow, for example initiated by movement of the applicator element over the said surface. The supply of fluid to the applicator element can for example result from adhesion of the product to the moving applicator element, from gravity, from capillary effect or from a combination thereof.

In other embodiments during use the product may be actively fed to the applicator element, for example with a controlled flow and/or with a controlled, preferably predetermined amount per period of time. Actively fed can be understood as at least meaning that a positive force is applied to the product for feeding an amount of product to the applicator element. This can for example be achieved by a piston, or a movable or deformable wall of the reservoir, acting on the product under the influence of a displacement source or power source, such as but not limited to a motor or pump.

Preferably the light source is provided in the housing. In embodiments the light source can comprise or be formed by one or more LED's. The light source can have different elements for different light frequencies. One or more light guides can be provided for guiding the light through part of the housing, from the light source to the capsule when mounted properly. A light guide can for example comprise one or more optical fibers or a light transmitting element or elements, such as an element, for example made of a transparent plastic such as but not limited to PMMA, Perspex, PC or the like, or of glass. The capsule can be provided with one or more windows or openings or be made of a light transmitting material, for allowing light from the light source cq light guide to pass into the capsule and/or into and/or through the applicator element and/or passed the applicator element.

The disclosure inter alia relates to a capsule (which can serve as applicator device) and a device which provides energy in the form of light radiation waves. The device enables at the same time the application of a product containing an active component or forming a cosmetic product, and light radiation of a wave length selected on or just below an application surface, in particular the dermis of a skin.

More in general, objectives of the present invention can be a) as desired, capsules of various geometries which allow the application of several different products or with an optimized preservation capacity, or further still with an optimized quantity, and b) a combined device allowing:
at the same time, the distribution (or spread, and preferably application, hence putting on) of a product, containing an active component or forming a cosmetic product, on a surface of a living body,
and the discharge of energy in the form of (a) light wave(s), via for instance electroluminescent diodes (LED's) passing from UV to infrared, thus creating an interaction between product and energy, on or below the said surface.

Also envisaged is:
a capsule with which the field of application of the device can be enlarged, in particular for treatment of the skin,
and a device which improves a synergic reaction in or on the epidermis, between radiation and an activation of the product.

It is understood that here, 'product' is understood to mean a substance, containing an active component or forming a cosmetic product. What is concerned here is a product for local (topical) application, which is either a cosmetic product, or a medicine, with its (their) active component(s). It has a more or less fluid consistency and composition, with a possibly variable viscosity and texture according to the sought after benefits. A serum can be involved, or a liquid emulsion, without excluding slightly thicker consistencies, if necessary. Preferably, the active component has a bio-inductive effect.

Advantageously, the product contained in the capsule can be such that it reacts to a given wavelength and a given time of exposure to radiation.

An object of the present invention is a solution with which the substance to be applied is optimally protected, to select the substance depending on the application to be considered, while always benefiting, on the entire device, from the light radiation which is favorable to the efficiency of the product, once it is applied.

In addition to the skin, the distribution surface for the product can be the external surface of a living organ, in particular an organ that needs to heal.

The proposed capsule can be such that it provides a product distribution zone, and comprises: in a body, a supply of product which is in communication with the distribution zone of the product, and first linking means, and second linking means, for removably connecting, between the capsule and a housing in which is disposed a light source. The first and second linking means can be situated at a distance from the light ray(s) coming from the light source.

The exchangeability of the capsule, and therefore the changing of product is thus improved.

Another advantage is, if desired, that a capsule is provided which can be used once (mono-dose), and is especially hygienic as thus, the risks of proliferation of bacteria and oxidation of the product (and of the active component in particular) are restricted. Furthermore, the same housing can receive various capsules, especially having different forms and/or content.

To simplify the way of activating the product or the bodily environment where it is placed, it is recommended that preferably, the emitted ray(s) pass through the product distribution zone mentioned.

For a given product, it is possible to reduce the exposure to radiation (filtering of the rays on the capsule) by regulating the focal point while changing the optical indexes of the transparent parts of the capsule, modifying the diameter of the ellipsoid of revolution that can serve as applicator element (see element 7 hereinafter), which diameter can be adjusted depending on the viscosity of the product and/or modifying the supply of product under the ellipsoid of revolution (in particular ball), again depending on for example the viscosity.

It is further recommended that the device comprises product applicator means, for applying the product application (putting it on) on said surface, and means for starting the emission of the ray by the light source, while these starting means are activatable by the user at a distance from the distribution zone and/or with the intermediary of applicator means for allowing the start of the emission while the product is applied via said distribution zone, favorably such that then, the ray passes through the applied product.

Furthermore, the safety of the user with regard to the emitted light can be checked.

In order to improve a uniform distribution of the product and its penetration into the thickness of the dermis or the surface of the organ, which is a priori porous, it is recommended that the capsule comprises a movable element having an outer wall, preferably convex, which contributes to or ensures the product application, and/or which is movable on said surface by the intermediary of the distribution zone of the product.

This is advantageous to the compactness of the device and to an interaction between the application of the product and a possible "massaging" effect favorable to the penetration thereof into the surface, which is porous.

In preferred embodiments an applicator element is provided in or on a cartridge having a relatively hard surface for contact with the skin of a user, forming or containing a product distribution zone. In this disclosure relatively hard should be understood in relation to skin of a human body. Relatively hard may be understood as meaning at least but not necessarily limited to not spongeous. Relatively hard may be understood as meaning at least but not necessarily limited to having a surface hardness which is such that when the surface of the applicator element is pushed against the skin of a user during application of a substance contained in the cartridge, the skin will be compressed by the applicator element more than the applicator element by the skin. Preferably the applicator element is sufficiently hard not to be compressed during application, when a normal force is applied to the skin by the applicator for applying the substance.

In preferred embodiments an applicator element is provided in or on a cartridge which is relatively rigid, for contact with the skin of a user, forming or containing a product distribution zone. In this disclosure relatively rigid should be understood in relation to skin of a human body. Relatively rigid may be understood as meaning at least but not necessarily limited to having configuration which is such that when the surface of the applicator element is pushed against the skin of a user during application of a substance contained in the cartridge, the skin will be elastically compressed by the applicator element substantially without deformation of the applicator element.

In preferred embodiments an applicator element is provided in or on a cartridge which is non absorbing and non permeable for the substance contained in the cartridge, such that during application the substance will be distributed over at least part of the surface of the applicator element but does substantially not penetrate into said surface.

In order to improve the interaction between the delivered light energy and the applied product, it is advised that the light source emits the ray(s) towards the surface, through the distribution zone.

In order to provide a proper distribution of the product over a skin area, preferably an active product supply is provided for ensuring a constant flow of product to the applicator element for distribution.

To reduce oxidation and dehydration of the product contained in the device, it is recommended that prior to the first distribution, a protective foil or cap is provided over the movable element.

In order to optimize the application of the product as well as the passage of the ray as far as the surface mentioned, it is recommended that the device provides an axis along which the ray is emitted towards the surface, while the product supply is situated either at least essentially transversely to the axis mentioned or around this axis. In the first case, the ray does not pass through the product, and in the second case, it does. This should be taken into account in determining the focal point.

To further improve the application of the product without disturbing the passage of the emitted light ray(s), it is advised that the movable element provides the product distribution zone. Thus, the synergy product/light can be improved.

Still with respect to a favorable distribution of the product and this synergy, it is recommended that the movable element pivots about at least one pivotal axis and has a convex exterior wall, and/or that the movable element has an ovoid form, preferably an ellipsoid of revolution, and pivots on the body, and/or rotates in the body.

For protection of the product, without this interfering with the removable connection between the capsule and the body of the device bearing the light source, or with the favorable emission of the ray(s), the capsule can have a cavity which is open towards the exterior to one side and have a blind flange, preferably transparent to rays, said first linking means of the capsule being situated towards this blind flange, and lateral relative thereto.

Thus, at the same time, it is ensured and simplified both the separation and the axial connection between the housing bearer of the light source and the capsule, without hindering the free passage of the light rays/radiation.

With respect to the device itself, it is understood that it is provided with the precited distribution capsule, and the housing to which this capsule is therefore secured in a removable manner, by first and second linking means, and in which is disposed the light source adapted to emit, toward the product distribution zone, and therefore the distribution surface, the light ray(s) or at least one wavelength.

For reasons already given, it is recommended that the light source emits ray(s) through the product application means, and preferably, that the product applicator means comprise, as movable element, an ovoid form through which the ray(s) can pass. Thus the above-mentioned synergy is improved and with this ovoid form, preferably an ellipsoid of revolution, an optical system can be created. The ovoid form in its housing can be arranged to adapt to the viscosity of the substance.

In a favorable embodiment, for a simple and efficient optical system, the optical index of the movable element is constant over the entire mobile element, which is uniformly solid or hollow.

The movable element can be designed from different materials, solid, hollow or liquid. Thus, in embodiments the focal point can be regulated to a certain depth in the surface, in particular the epidermis, so as to optimize the effect of the chosen product. With the same purpose, the dimensioning of the ovoid form and in particular its diameter and the distance relative to the source enable regulation of a focal distance and concentration of the light flow to a certain distance below the application surface concerned, in particular the dermis, if light is to be emitted at least partly through the movable element.

Again for the performance of the synergy between the application of the product and the effect provided by the radiation, it is recommended to limit the oxidation of the product while considering the device as a whole of two parts comprising a housing in which the light source is accommodated and a capsule, movably secured to the housing and containing the supply of product and the product distribution zone. Thus, the capsule can be a recharge/refill which allows the use of a disposable, one-time-dose of product. The amount of product can then be a one day dose of treatment.

The dose of product contained in the capsule can be especially protected against oxidation by the packaging formed by the capsule, while removal of a sealed protective film or cap only takes a few seconds just before the application of the product.

Alternatively, or preferably additionally, a lid is provided in a removable manner, for isolating the supply of product from the environment, whereby a volume is covered at an atmosphere intended to protect the product from oxidation prior to the first opening of the lid.

For the transmission of the ray towards the surface and the protection, a first wall transparent to the ray can be provided, interposed between the light source and the product distribution zone, and which allows the ray to pass through this zone. This wall can be dimensioned such that is sufficiently great for allowing the ray(s) to concentrate on the zone of the exterior, convex wall of the movable element that comes into contact with the surface of the body, or beyond.

In this respect, it is favorable for the efficiency of the synergy between the applied product and the ray emitted towards the application surface, that the passage of the ray in the optical system formed in the device concentrates this ray in the contact zone, there where the product distribution zone comes into contact with the surface to be treated, or slightly beyond, more deeply into this surface.

In this respect, a well chosen solution is a priori a solution where the movable element having the distribution zone and/or the supply which feeds it with product, define an optical device as such, while the application means are in contact with the surface of the body, the passage of the optical rays in the device concentrate these rays in the contact zone. The movable element can be integrally formed to concentrate the ray(s) on or a few millimeters beyond the distribution zone mentioned, which is a contact zone with the surface of the body in a manner such that, with the distribution surface being the skin. A focal point can be located in the dermis or, between the dermis and the epidermis. In embodiments the light can be distributed over part or all of the contact zone between the movable element, such as a ball, and the surface for application, such the skin. In embodiments the light can be distributed over an area around the contact zone between the movable element, such as a ball, and the surface for application, such the skin.

If the solution with a disposable capsule is considered, it is further recommended that the first wall transparent to the ray be airtightly secured to or form an integral part of the capsule with respect to the product. This especially increases the protection from oxidation.

A disposable capsule should be understood as a capsule which is to be replaced by another such capsule each time its supply of product is exhausted. A disposable capsule is preferably a capsule which cannot practically be filled again after use.

In the housing, the light source can be protected by a second wall transparent to the ray which, with the capsule and housing assembled, can be situated opposite to the first transparent wall. In principle, only air separates the opposing first and second walls.

To promote the use of the device on numerous locations of the surface in question, as well as the spread of the product on the movable element, it is further recommended that this movable element be ellipsoid of revolution, in particular a sphere or a more oval form, pivoting in all directions, in or on the device. Preferably the element is a ball.

For the use and the ergonomics of the solution proposed to the user, it is advised that the housing of the device provides for a push-handle for moving the movable element, this push-handle extending in a direction towards the movable element and batteries or a feed battery for the light source which are arranged in the push-handle. The housing can be designed as the push handle, meaning that the device can be held by the housing and be moved over a skin surface by for example rolling the movable element, such as the ball, over the skin.

For safe use, and taking into account the light intensity of the ray which might damage the retina of a user when catching the ray, it is provided, while ensuring a simple functioning of the device and avoiding unnecessary loss of electric energy, that on the device, starting means for the emission of the light by the light source are provided which can comprise a first body, mounted with the application means and itself translatably mounted along an axis relative to a second body of the device, between a first position where the first and second body are axially distanced one from the other while opening (interrupting) an electric circuit comprising the light source which, in this manner, cannot emit a ray, and a second position where, by pushing the movable element along this axis, the first and second body are axially brought closer to each other while closing the electric circuit so that the light source emits its ray, and biasing means, provided between the first and second body for returning them in a natural manner to the first position. Thus, pressure on the movable element starts the electric contact, and switches on the device. Light will be emitted only in the event of a pushing motion on the movable element. In rest, no light whatsoever will be emitted. This, preferably together with the presence of an opaque protective lid movably mounted on the movable part forming the applicator of the product, allows for combining proper protection of the product in supply (via the lid) and safety of use, wherein there will be emission of light only if, with removed cap, the movable element is pressed in. If not, the starting means comprise an interrupter on/off and preferably the above mentioned protective cover.

With respect to the manner of distribution of the product on the surface involved and the emission of radiation, it is advised for reasons already given hereinabove, that the method comprises application of the product on the product distribution zone of the device mentioned, and the emission of radiation towards this distribution zone, preferably together with the application of the product.

To improve the synergy between the distribution and the emission of radiation, while simplifying the use, it is recommended that the product be provided in a product supply of the device, that the product is distributed by rolling a movable element of the device, in contact with the product in the product supply, and that, by a light source of the device, a surface of an exterior wall of the movable element be lighted, through the movable element.

However, for certain products and certain applications, it is provided that the product can easily be placed in the luminous path, whereby the focal point is modified and the reaction of the cells is improved.

The bottom of the capsule is designed in a material transparent to the radiation, or can be optically filtering, which allows for the selection, on a given capsule, of wave lengths adapted to the conditions of use. It is advised for a specific product, for an identical wavelength emission of the light source device to provide the light source emitting rays in a housing of the device,—to provide the product in a product supply of a capsule comprising product application means, and also associated to the device, whereby the capsule forms an optical system, to movably secure the capsule to the housing and to modify the refraction index(es) of the optical system of the capsule traversed by the ray, depending on the product, for example for and/or changing the emitted light frequency changing the focal point.

For reasons of ergonomics and ease of handling of the device, it is recommended that, with the capsule secured to the housing, the housing has a push handle for moving the movable element, while advantageously extending in a direction towards this movable element and the light source, and wherein the feed batteries of the light source are arranged.

To check the interaction between the produced light energy and the distributed product, and/or the safety of the user with respect to the emitted light, it is recommended that starting means are provided, activatable by the user at a distance from the distribution zone and/or by the intermediary of the movable element, thus allowing for the start of the emission of the ray by the light source when the product is distributed via the distribution zone mentioned, so that the light flow passes through the distributed product.

With respect to distributing the product over the surface concerned, and creating warmth and/or photonic activation of the constituent cells of this living surface, by light radiation thereon, it is provided to distribute the product on this surface, via the product application means, and, preferably simultaneously, to emit towards this surface the radiation coming from the light source, while adapting the focal point thus that photo-biomodulation is effected, which preferably penetrates as far as the fibroblasts responsible for the production of collagen and blood vessels.

To reach the surface to be treated, the radiation coming from the light source can pass through the application means and in particular the movable element. However, another configuration can be envisaged: have the ray(s) pass alongside the applicator element, in particular around, via for instance a series of electroluminescent diodes disposed in a circle.

Figure 1:
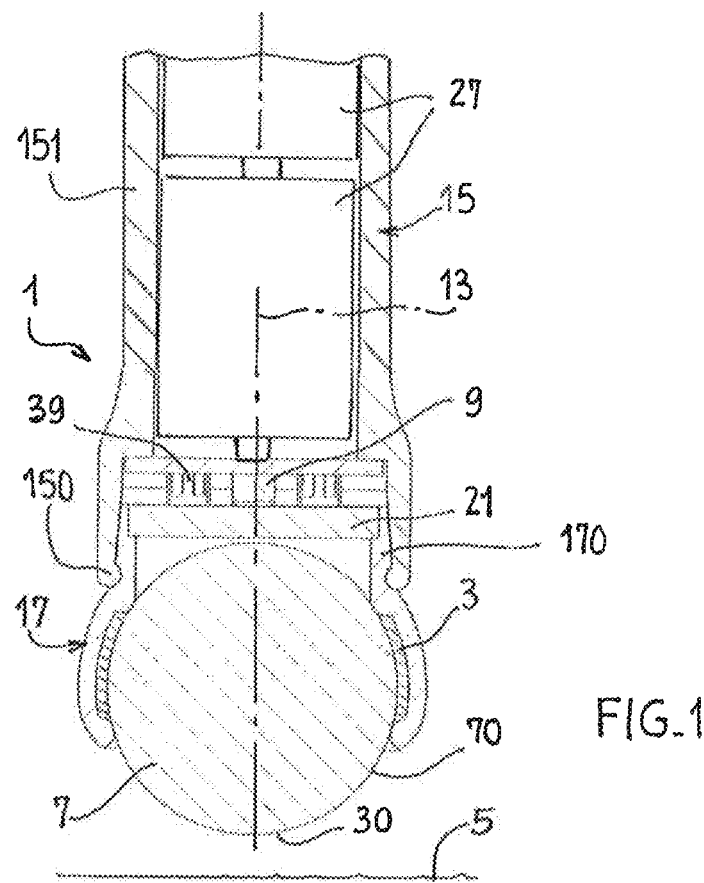

FIG. 1 shows a distribution device 1 of a product 3 of the mentioned type, on a surface 5 of a living body and the discharge to the surface 5 of energy in the form of light ray(s) or illumination of this surface.

The product 3 contains an active component or forms a cosmetic product.

It is preferred that it has the consistency of a liquid or a crème.

The surface 5 can be skin surface, or (epi)dermis. Also, the surface of an organ of the human body can be involved, including in internal organ accessible through operation, and which can be healed. More in general are involved cutaneous applications, treatment of acne, stretch marks, cicatrization, such as but not limited to skin or internal organs.

The device 1 has a zone 30 of distribution of this product to the surface 5, there where product is present and where it can be in contact with the surface to be covered.

For distributing the product and optimally activating it, the device 1 can comprise:
an applicator means 7 having a rounded exterior wall 70, and a light source 9 consisting of or comprising an emitter of one or several rays 90 towards the surface 5, preferably through the element 7, having a convex exterior wall 70.

Advantageously, the applicator element is movable in and/or on the body of the device.

Advantageously, the source 9 comprises one or several electroluminescent diodes. They can emit light according to different wavelengths, thus allowing an adaptation of the effect on, or in, the surface 5, preferably depending on the product 3.

Here, the product 3 is liquid and rather fluid. Preferably, it has a viscosity that allows the product to be spread substantially uniformly over the distribution zone, during the exposition time to (a) selected illumination/(light) wave length(s).

The movable element is preferably ellipsoid of revolution ovoid, in particular a ball, whereas preferably the ray(s) can pass through it.

Here, a solid, transparent glass ball or solid polymer ball, or containing another product, solid or liquid can be involved. Alternatively the ball can be a hollow ball, for example a plastic ball.

In a preferred embodiment, the ball allows the passage of wavelengths between 400 and 1400 nm. Its diameter can for example be between 8-12 mm, although it can be smaller or larger.

A filter color can be added to the device, for instance to the movable element such as the ball, for selectively avoiding the transmission of certain wavelengths to the surface, this to augment the efficiency of a specific product, or for protecting it.

This movable element is pivotally mounted about at least one pivotal axis and it can be seen in the drawings that it is preferred that the exterior wall 70 has a convex exterior.

Although for instance a cylindrical or ovoid shape is possible, with, in that case, a movable element 7 mounted a priori pivotally around a single rotational axis perpendicular to the direction 13, it is recommended that the movable element 7 be ovoid, preferably an ellipsoid of revolution, has an ovoid shape such as a ball pivoting freely in all directions, in or on the device.

This improves a substantially uniform spread of product 3 and of the light on the surface 5, whatever the orientation in space of the device may be relative to the surface 5. Advantageously, the ellipsoid of revolution or ovoid shape, especially ball shaped, has a diameter which allows it to pass over all the parts of the face.

The device 1 also comprises a supply 11 of product which is in communication with the distribution zone 30, here the movable element 7.

In this respect, it is recommended that the product distribution zone 30 is situated on the movable element 7, here, in the Figures, at the surface of the exterior convex (rounded) wall 70.

To avoid ray/product interference to a high degree, it is recommended that the supply of product 11 is situated transversely relative to the axis 13 parallel to the direction the ray 90 is initially emitted in, towards the surface 5. But this is not necessary: provision in a rear zone, behind the applicator means 7 is also possible (see zone 11a in FIG. 2, or 11 in FIG. 7 and following). In FIG. 12-15 further possible positions and solutions for the supply of product are discussed. In this respect it should be noted that supply of product may be understood as being formed by or comprising a reservoir 102 for product 3.

Figure 6:
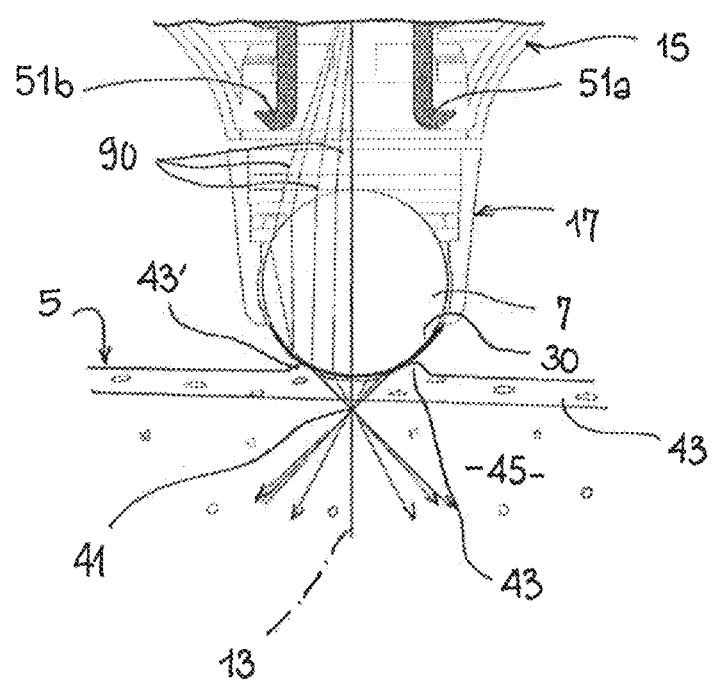

To further improve the synergy between product and emitted ray(s), it is recommended that the passage of the light or optic ray 90 in the device concentrates this light in the zone 25 where the exterior, convex wall 70 of the movable element 7 comes into contact with the surface 5, or some millimeters beyond, as shown in FIG. 6. Alternatively the design may be such that the light is spread over a wider surface area, for example by refraction by the ball 7 and/or by other parts in or of the housing 15 and/or capsule 17, as indicated in e.g. FIG. 3.

With respect to FIG. 6, the point 41 where the energy is the greatest is the location of the optical focus defined by the refraction indexes of the whole of the optical system. This focal point can be modified on the exchangeable capsule 17 (see further), for increasing the efficiency of a product, through changing the refraction indexes of the optical path, i.e. by modifying the materials, or by designing parts in different materials.

Still with respect to FIG. 6, it is clear that the distribution zone 30 of this product, here the exterior surface of the movable applicator 7 applied on the epidermis 43 of the skin of a patient, has a massaging effect on this epidermis, shown as for example small bumps 43', and improves the depth penetration towards the dermis 45 of the product that covers this surface.

Especially when the focal point 41 is in the dermis, the emitted light can be infrared light.

On the device, optionally, flexible ring-shaped lips 19a, 19b can ensure the airtightness before and behind, respectively, the supply of product 11, i.e. reservoir 102, while allowing passage only to the front at 19a of a film of product around the movable element 7, in the way of a wringer. The clearance allowed by the lip 19a matches the viscosity of the product. The discharge and the spread of the product 3 on the surface of the movable element 7 can be performed through capillarity. The movable element 7 can be mounted by snap connection in the supply space 11, i.e. in the housing 110.

In order to simplify the design, it can be preferred that product can pass between the movable element 7 and the bottom of the supply 11, here the wall 21.

Additionally, the device is provided with a housing 15 which can form a push handle in which is accommodated the light source 9 to which is preferably movably secured a capsule 17 comprising a supply 11 of product and the movable element 7. This can simplify the use of a single use capsule 17 which then becomes a disposable, which can be disposed of after use.

Hence, capsules can be exchanged or replaced and therefore especially provide several products to be applied, or diffuse several rays, for instance while having various movable elements 7. Diffusing several rays shall be understood as including the possibility of changing the color of light passing through the capsule due to differences in refraction indexes, coloring of the ball 7 or the housing, providing refraction elements such as but not limited to Fresnel lenses or prisms or similar means for influencing the light.

In this way, the capsules 17 become replaceable, especially disposable, refills, so that the use of one-time doses of products such as different serums, is made possible. The reservoir 102 of a capsule 17 can for example hold a small amount of product 3 to be dispensed, which can for example be less than 10 ml, more specifically less than 5 ml, more in particular less than 3 ml, such as for example between 0.01 and 1.5 ml. Other volumes are obviously possible.

The supply 11, i.e. the reservoir 102 is provided in a body 110 of the capsule relative to which the applicator element 7 is movable.

Between the light source 9 and the movable element 7 is interposed a first wall 21, transparent to the ray which it allows to pass, towards the movable element. In particular in FIG. 1, the wall 21 is perpendicular to the axis 13, as e.g. shown in FIG. 1.

It is recommended that this wall 21 be transparent to a wavelength of between 400 nm and 1400 nm, preferably such that, it substantially does not alter the optical characteristics of the radiation and/or that it has a size and shape sufficiently great for a ray to concentrate on a defined focal point depending on the product and the desired effect (FIG. 6). Alternatively the wall 21 may have (an) opening(s) or window(s) for allowing the ray(s) to pass through.

Preferably, the transparent wall 21 is secured to or an integral part of the capsule 17 such that it is airtight to the product, thus giving this wall a double function. The light source 9 will then be in a zone isolated from the product contained in the supply 11 i.e reservoir 102.

Figure 2:
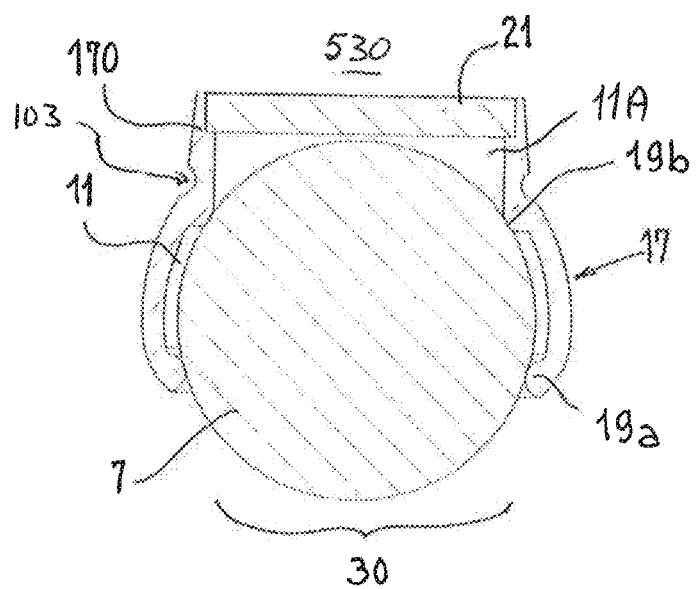

To simplify assembly and disassembly and reduce the production cost of the two assemblies, the housing 15 and the capsule 17 can be snapped together through the lip 150 of the housing elastically retaining the rear top piece 170, via the peripheral groove 103, in the housing where also the transparent wall 21 is engaged. The lip 150 and groove 103 can form first and second connecting means or elements 100, 101. This is advantageous for assembly/disassembly in case only the capsule 17 is utilized. In FIGS. 1, 2 it is indicated that the linking means 150 of the capsule, in this example preferably formed by this peripheral groove 103 of the body 110, are situated towards the closed wall 21, laterally relative thereto, and therefore do not hinder the passing of the ray.

Figure 3:
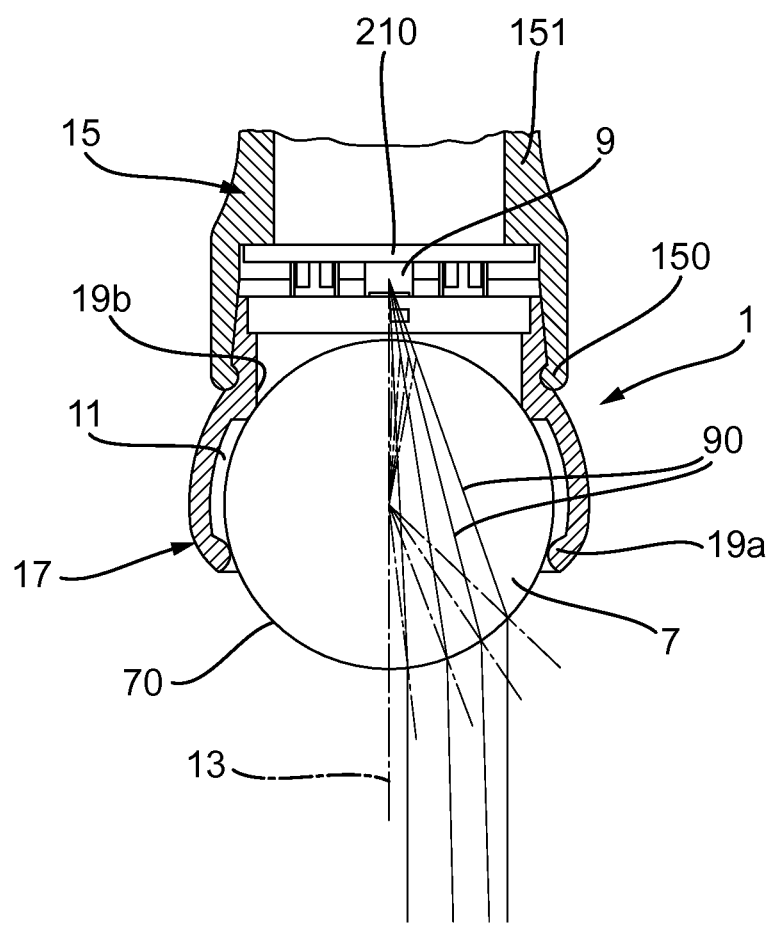

Further to the rear, especially illustrated in FIG. 3, in the housing 15, the light source 9 may be protected by a second wall 210, which may or may not be transparent to the ray from the light source 9 and secured to the inside of this housing 15.

With the capsule 17 and housing 15 in assembled condition, the second wall 210 is situated opposite the first wall 21.

Thus, the light source 9 is interposed between the first and the second wall 21, 210.

The two walls 21, 210 can be parallel to each other. The ray emitted by the light source 9 at a predetermined wavelength and which is emitted as far as the application surface 5, travels successively through the first wall 21, the applicator means 7, then the layer of product 3 discharged on the surface 30, each having its own refraction index.

Advantageously, the applicator means 7 defines an optical system. This can be hollow, with air in the interior, or any substance in solid, liquid or gaseous form, so that the focal point can be placed anywhere one wants at the exit of the capsule.

For a good hold and easy handling after application of the product, it is advised that the housing 15 comprises or forms a push handle or casing 151 for moving the movable element. Advantageously, this push handle extends in a direction, here 131, towards the movable element/applicator means 7.

In the housing 15, in the push handle or casing 151 are disposed one or several electrical feed batteries 27 of the light source 9 or a connector to a mains.

Incidentally, for safety of use and long lasting functioning, it is recommended that the movable element 7 be mounted to or engaging a first element 29 of the device 1 which, in turn, is movably mounted for translation following an axis relative to a second element 31 of the device. The above-mentioned axis can be the axis 13 that passes through the source 9 and the movable element 7.

It is thus ensured that the starting means 47, started here, apart from the distribution zone 30, by the intermediary of the movable element 7, allow the start of the emission of the ray by the light source, while at the same time the product is applied through this distribution zone, such that the flow of light then passes through the applied product.

The fact is that the first element 29, bearing the movable element 7, is favorably mounted for translation between:
  a first position (FIG. 4) where the first and second element 29, 31 are axially distanced from each other while opening (interrupting) an electric circuit comprising the light source 9 which, then, cannot emit the ray, and
  a second position (FIG. 5), where, by the pressure of the movable element 7 on the surface 5, along axis 13, the first and second element 29, 31 are axially brought together while closing the electrical circuit such that then, the light source emits, preferably automatically, the ray 90.

It is preferred that a biased element 33 is provided between the first and second element 29, 31, to return them in a natural way to the first position, as is illustrated.

The first and second element 29, 31 are electrically conducive to form the interrupter 35 which is opened when the device 1 is in rest (the circuit comprising the light source 9 does not emit any light) and closed if a pressure according to the axis 13 is applied thereon (typically through a contact with the application surface 5). The light can be emitted in the movable element 7 with a slight delay controlled by an electronic decade of 39 (circuit delay FIG. 1), all this for security reasons.

What is thus prevented is that the light source emits a strong light to the eyes of the user.

Figure 4:
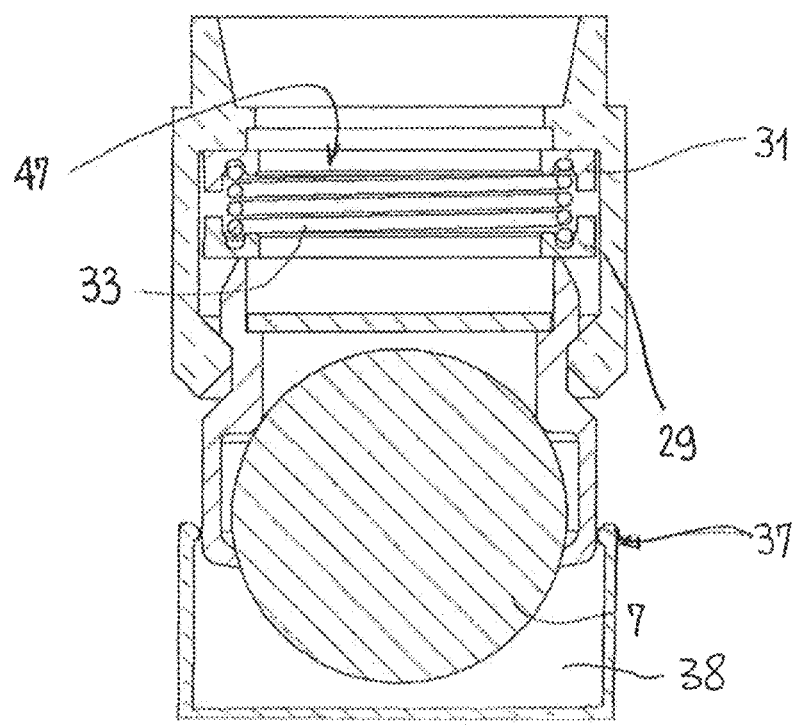
Figure 5:
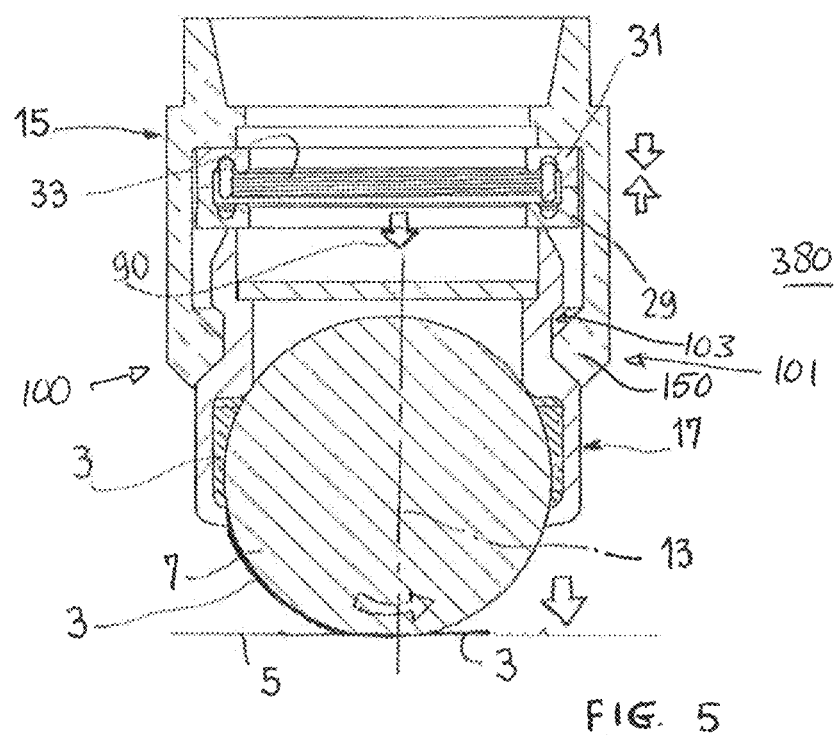

Alternatively the first and second coupling means 100, 101 of the capsule 17 and housing 15 are designed such that once the capsule 17 is properly coupled to the housing 15 the elements 29, 31 are brought into the conductive position, such as e.g. shown in FIG. 5, and only after removal of the capsule 17 from the housing 15 the electrical circuit will be broken, as e.g. shown in FIG. 4. An advantage thereof can be that the movable element 7, i.e. the ball, can also be moved lightly over the surface, still emitting light.

Preferably, a lid 37, advantageously opaque, and therefor in turn an anti-ray protection, covers the product supply 11 and is removably secured to the body of the device, preferably to the capsule 17. Mounted on the capsule 17, the lid 37 may or may not bear on the movable element 7 that it covers here. Preferably, it is robustly secured so as to prevent (or at least limit) the passage of air towards the internal volume 38 which it isolates, beneath it. Before the first opening of the lid 37, the air pressure in volume 38 can be lower relative to the exterior 380, or filled with an antioxidant substance aiming to keep the product 3 from oxidizing or limit oxidation.

Connecting it to a one-dose capsule 17 is particularly appropriate.

To adapt the device in particular to various types of application surfaces, for instance skin, it is provided that the light source 9 can generate different wavelengths, alternatively or simultaneously during a continuous contact between the movable element 7 and the surface 5.

During such a phase of, at the same time, discharge of the product 3 on this surface and illumination thereof by the light emitted by the light source 9, the generated light beam can be modulated in intensity or sequence during contact.

As already indicated, the reservoir or supply 11 can extend between the movable element 7 and the light source 9. This would then imply that the refraction index of the product 3 should be taken into account. The product 3 to be spread then forms an integral part of the optical system, its refraction index being taken into account in the optical sum.

However, this is not advantageous if the quantity of the stored product 3 in the device, especially the capsule is reduced, the more so as one risks less uniform (or non-uniform) distribution of the product 3. Furthermore, restricting the amount of product 3 in the radial periphery of the supply 11, transversely to the axis 13, could allow for omission of the rear wall 21.

Advantageously, the movable element 7 has such dimensions that, for optimal application on the skin, it can travel on all parts of the face, in particular also around the eyes. In a preferred embodiment, through rotation generated by friction on the dermis, the movable element 7 applies the product a priori obtained by capillarity from the reservoir 11.

In FIGS. 7-11 is shown a device 1 where, by mechanical deformation of the hollow piece 49 mounted in the housing 15, it is possible to axially (axis 13) separate this housing and the capsule 17. To this end, movable brackets 51*a*, 51*b* are borne laterally by the deformable part 40 and are mounted pivotally or deformably relative thereto. An internal passage 490 passes along the axis 13 all through the deformable piece 49. This internal passage provides, parallel to the pivotal axes 510*a*, 510*b*, lateral bearing surfaces 53*a*, 53*b* which are diametrically opposed relative to each other and accessible to the user on the housing, perpendicular to the axis 13. Thus, by pressing on these bearing surfaces, the hollow piece 49 is deformed transversely to the direction of pressing, and to the axis 13 and thus the brackets 51*a*, 51*b* are pivoted from a position naturally apart from each other along the direction of deformation to a position closer together so that the capsule 17 can be secured and/or removed relative from the housing.

Figure 7:
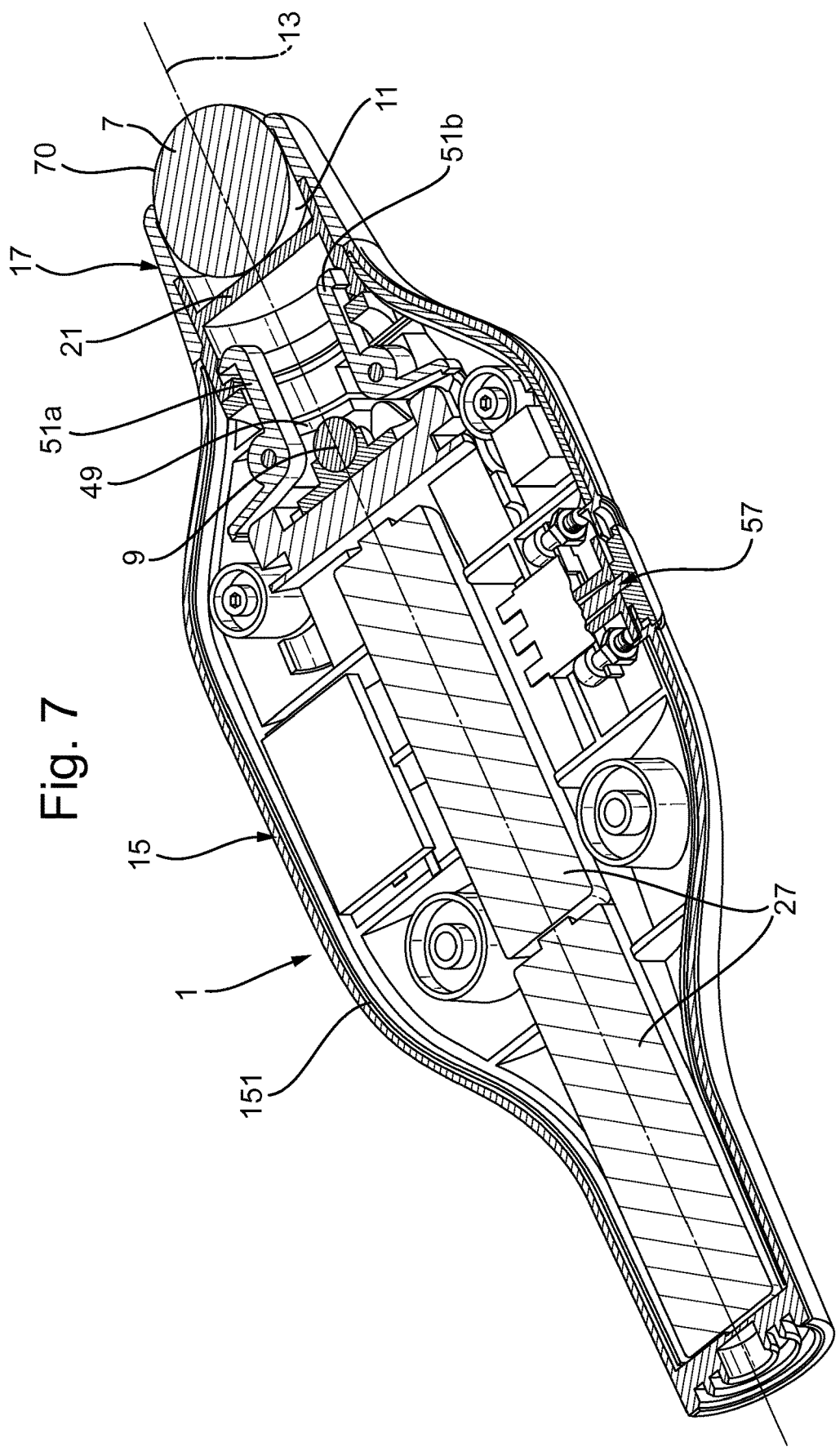
Figure 8:
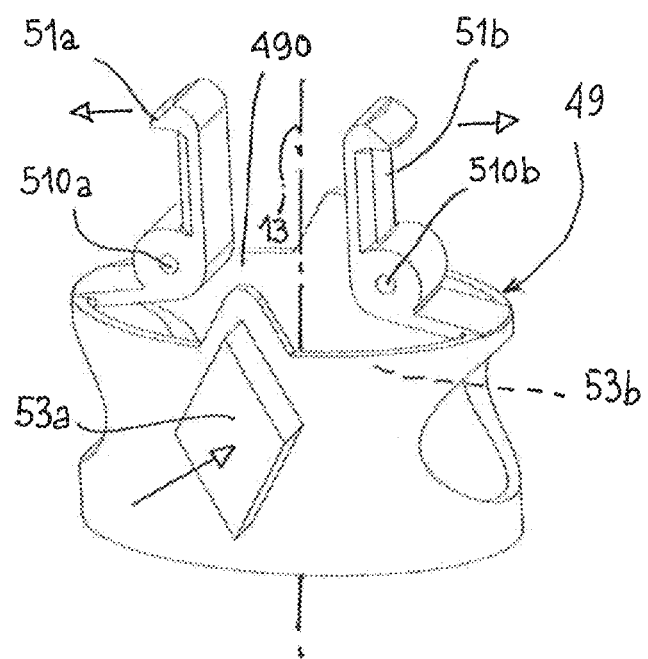

Additionally, as is shown in particular in FIGS. 7, 8, the capsule 17 comprises linking means 52, forming first coupling means 100, for ensuring the desired removable fixation between the capsule 17 and the second linking means 54, forming second coupling means 101, of the housing 15, the first and second linking means being situated at a distance from the zone of passage of the light ray coming from the light source 9 and passing to the product application zone 70.

More specifically, the capsule encloses a cavity 53 which:
is open at one side towards the outside at 530 (opposite the movable element 7),
has a wall 21 that separates it from the supply 11, and
comprises a side 55 around an opening of the cavity 53, the side belonging to the first linking means 52 or first coupling means 100, so that there are removably received the movable brackets 51, which belong to the second linking means 54 or second coupling means 101.

Figure 11:
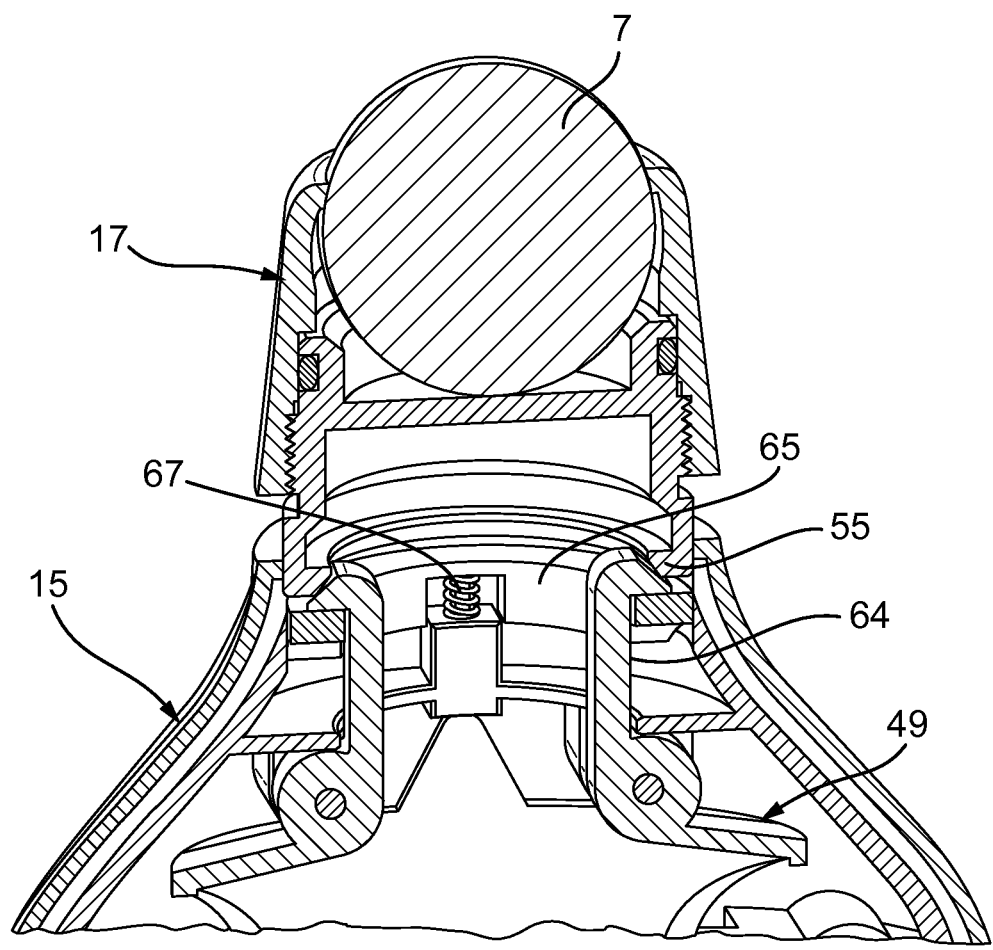

To improve the engagement of the side 55 which is annular here, under the end 511*a*, 511*b* curved towards the interior of the brackets 51*a*, 51*b*, these latter provide biased inclinations with complementary inclinations at the inside periphery of the side (see FIG. 11 for the guiding of the inclinations which effects the brackets 52 to approach one another).

Figure 9:
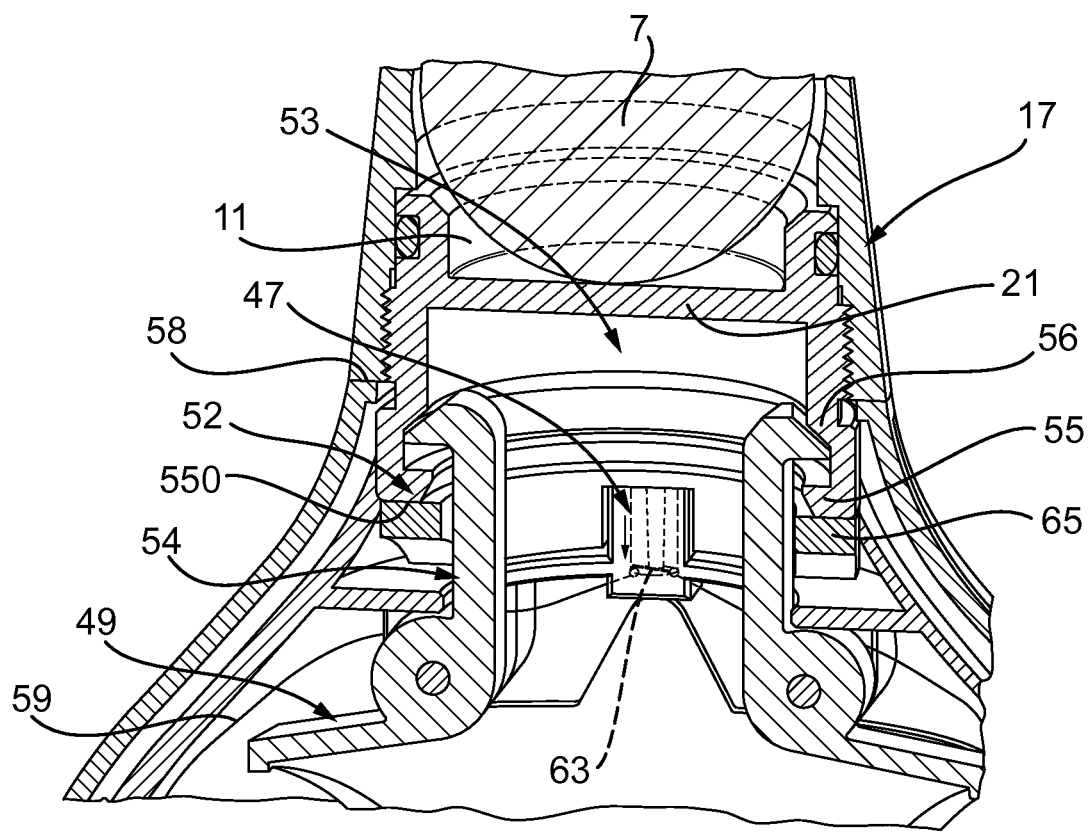
FIGS. 9, 10 and 11 show enlarged zones of the device of FIG. 7 in interior view.
Figure 10:
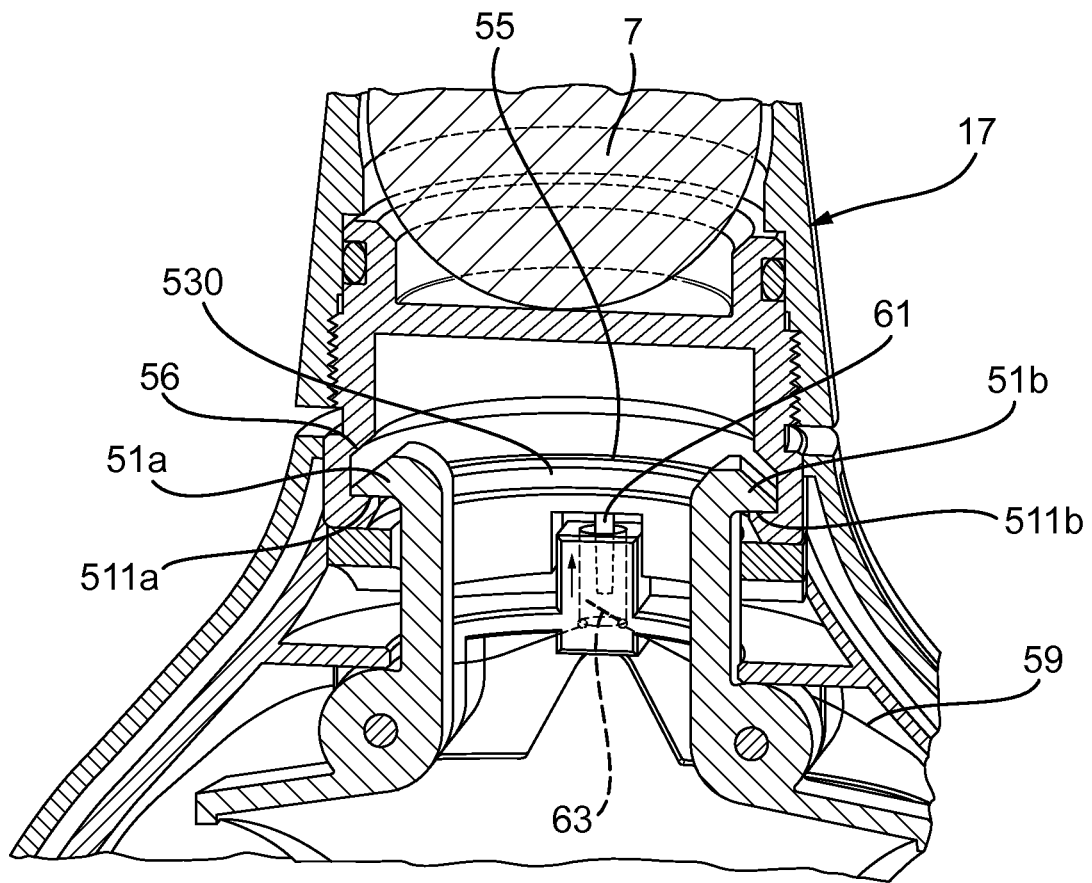

In FIGS. 7, 9, 10, it can be seen that with the capsule 17 secured in the housing, the starting means 47, 58 enable the start of the emission of the ray(s) by the light source 9, while it should be specified that the solution of FIGS. 1-5 favorably comprises a means 57 comprising an on/off interrupter which is at all times accessible to the user from the outside of the housing. The interrupter 57 is connected to the light emitter 9 so that the light emission is started at the closure of the interrupter.

If, now, in FIGS. 7, 9, 10, the starting means 47 is actuated as before by the pressure of the movable element 7 on a support, via the surface 70, it is preferred that this means 57 also comprises the interrupter 63 on/off accessible from the outside of the housing 15.

With regard to the functioning of the starting means 47, if this 57 is in "go" position, it is provided, with the capsule 17 is secured to the housing, this capsule has once more the capacity to move relative to the housing 15, through a displacement (translation) according to the axis 13, for:
c) in a first position (FIG. 10), opening the electric circuit 59 which comprises the light source 9 and the battery 27, and
d) in a second position (FIG. 9), closing the electric circuit, so that the light source can then emit light ray(s).

Thereto, a mechanical action can be chosen, on an internal interrupter 63, of a foot 61 connected to a ring 65 which is held in the opening 64 of the housing through which pass the brackets 51*a*, 51*b*, in the direction of the capsule.

Under the effect of the displacement of the capsule 17, according to the axis 13, produced by the pressure of the movable element 7, the ring 65 comes to press on the internal interrupter 63, via the projecting foot 61.

As can be seen in FIG. 9, preferably, an outside wall 550 of the capsule (here the base of the side 55) presses on the ring 65.

To secure the whole, the housing is furthermore provided with biasing means 67, such as springs, which return the capsule in a natural way to the first position, the interrupter open (FIGS. 10, 11). Thus, pressure on the internal interrupter 63 produced by the axial pressure of the movable element 7 will act against the stiffness of the biasing means 67.

Thus, the capsule 17 can move along the axis 13 relative to the housing.

Here, the guiding and one of the axial stop means are provided through lateral brackets 51*a* 51*b* which are located parallel to the axis 13.

Engaged in a groove formed perpendicularly to the axis 13, between the annular side 55 and an interior shoulder 56, the lateral brackets move there over a short axial distance. Preferably, also an annular exterior stop means 58 for the housing/capsule is provided.

With respect to the aspect "impact" on the surface 5 of a living body of the distribution of the product 3, together with the transmission of light towards this surface, it should be noted that the object is to achieve photo bio-modulation. What is involved here is stimulation through a row of photons (along the emitted wavelengths). For the skin it is recommended that it penetrates as far as the level of the dermis, or the hypodermis, the cells of the dermic matrix and in particular fibroblasts responsible for the production of collagen and blood vessels (collagen being the principal component of the skin, in particular responsible for its firmness and tonicity.) The stimulation of the blood circulation provides for an optimal feed of oxygen and nutriments to the cells for an improved functioning thereof.

Preferably, the radiation of the source 9 towards this surface 5 comprises infrared rays, a source of warmth.

As to active substances, in particular the following are provided:

ACS III, with molecular formula C37H69NO5,

INIC: Dipalmitol Hydroxyproline

Collagen synthesis enhancer Type III

An active ingredient for (human) skin care, which selectively enhances the synthesis of the isotope III of collagen A "transporter" liposome containing dipalmitate hydroxyproline covered by hydroxyl proline which acts as a modulator of the phenotypical expression of the fibroblast.

Collatein

An induction of HSP 47 accelerates the extracellular transport of the pro-collagen III and the folding of the alpha chains of the collagen during the synthesis of collagen and its externalization before the extracellular fibrillogenesis.

HSP 47 which are chaperone proteins specific for the synthesis of collagen.

In the context of a therapeutic treatment or a cosmetic indication of product 3, together with the emission of the precited rays, it is clear from what precedes that preferably, conditions for use are as follows the product is applied on the skin, via the distribution zone 30 of the device, and preferably simultaneously, a light radiation is emitted towards the skin, at the location of this distribution zone, while a focal point is used such that a photo bio-modulation is created that penetrates as far as the dermis, or as far as the hypodermis, the cells of the dermic matrix and in particular the fibroblasts responsible for the production of collagen and the blood vessels.

In the preceding examples, the distribution zone of product is limited to the surface of the applicator element 7. But, as is already mentioned, it can be provided that the light energy transmitted by the source 9, via for instance a series of electroluminescent diodes can pass sideways and in particular around the applicator element 7 before it reaches the surface 5. In this case, all or a part of the light energy will not pass through the applicator element 7, nor more generally the application means of the product, as they are. The important thing is that the energy, produced here in the form of (a) light wave(s), arrives on or in the surface 5 on which the product 3 has been applied.

It is clear that although the distribution (therefore the spread) of the product on the surface 5 is performed by the movable element 7, if, as is preferred, such an element is present also. The application of the product on the surface can be performed in another way, for instance by an associated distributor, separate from the device 1.

Thus, whatever the embodiment, a product containing an active component or forming a cosmetic product is distributed on a surface 5 of a living body, where it is activated, preferably simultaneously with its application, by the transmission to the cells situated on or in this surface of at least one wavelength in the form of a ray of energy.

Figure 12:
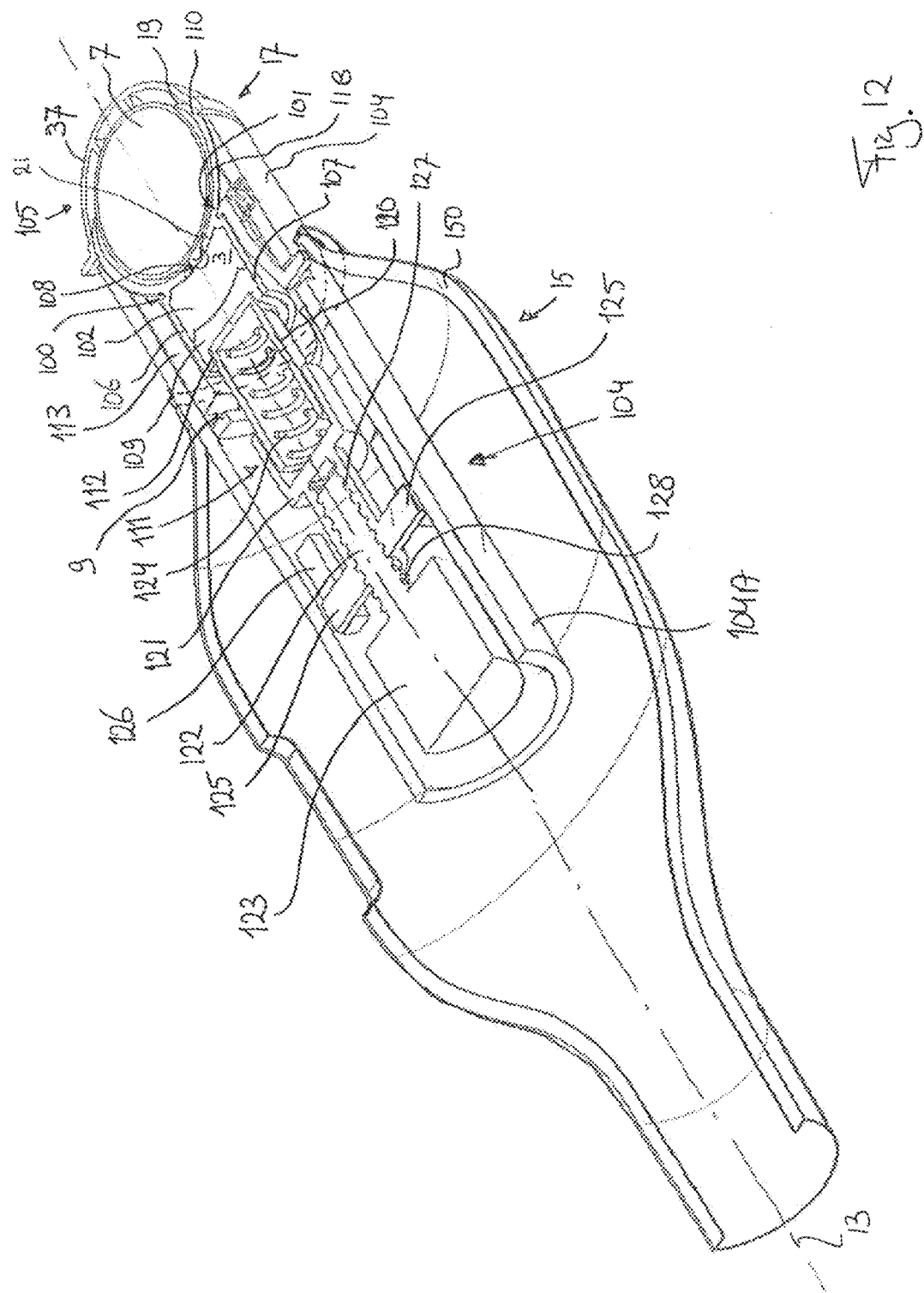
FIG. 12 shows in perspective view schematically a device according to the present invention, in cross section along a mid-sectional plane comprising a longitudinal axis, for actively dispensing of product.

FIG. 12 shows schematically in perspective view a device 1 according the disclosure, for dispensing a product and light, as discussed, in cross section along a mid sectional plane including the longitudinal axis 13. The device 1 comprises, as in the further embodiments as shown, a housing 15 and a capsule 17. The capsule 17 comprises again a ball 7 as applicator element, rotatably mounted in a capsule body 110, such that the ball 7 can rotate substantially freely in all directions. The capsule 17 comprises at least first coupling or linking means 100, for cooperation with second coupling or linking means 101 provided in and/or on the housing 15, as will be discussed further. By the first and second coupling or linking means 100, 101 the capsule 17 can releasably be coupled to the housing 15. The first and second coupling or linking means could as discussed with respect to FIG. 1-11, or as discussed hereafter.

In FIG. 12 the casing cq housing 15 is shown, in cross section, showing schematically part of the interior, including an active applicator unit 104, and a capsule 17. Further parts, such as batteries and circuitry for operating the device, as discussed before, are not shown for convenience sake. In FIG. 13-15 basically embodiments of the applicator unit 104 and a capsule are shown, which can be fitted in the casing or housing 15.

FIG. 12A shows schematically, in cross section, part of an active applicator unit 104 and a capsule 17, showing a general concept of active dispensing and light guiding. In FIG. 12A the ball 7 is shown, held by housing 110, such that it can rotate in all directions. Part of the ball 7 at a first side 105 of the housing 110 extends outside the housing 110, and can be brought into contact with a surface onto which product has to be supplied. At an opposite side the housing 110 is provided with a chamber or reservoir 102 for product 3. The reservoir 102 comprises a peripheral wall 106, preferably substantially cylindrical, defining an open end 107 opposite the ball 7. Between the ball 7 and the reservoir 102 a wall 21 is provided, with a relatively small opening 108 connecting the reservoir 102 with the space 11B around the ball 7. In the chamber or reservoir 102 a piston 109 is provided, sealing against the peripheral wall 106 in a known manner, for example by an O-ring or flexible sealing lip or the like, such that the piston 109 can be moved within the chamber or reservoir 102 towards the opening 108, along the axis 13. Initially the reservoir 102 will be filled with product 3 to be dispensed, preferably substantially entirely. The size of the opening 108 may be chosen, depending on for example the viscosity of the product, such that under atmospheric pressure at least at room temperature, for example between 18 and 30° C. or even higher temperatures, the product will be contained within the reservoir 102, even if held up side down, i.e. with the opening 108 facing downward.

When in such capsule 17 the piston 109 is moved towards the opening 108, product will be forced through the opening 108 and against the ball 7, in a volume equal to about the frontal surface area of the piston times the displacement along the axis 13, and thus well defined and controllable. If the ball 7 is pressed against the opening 108, the opening 108 may even be better sealed for keeping the product 3 inside the reservoir, for example prior to use of the capsule, whereas the ball can be pushed off the opening 108 by the product when the piston is pushed towards the opening 108. The ball 7 can for example be pressed against the opening 108 prior to use by a cap 37.

In embodiments the ball 7 can be held in the housing 110 without seals closing a space between part of the ball surface and the housing 110. In embodiments the housing 110 can comprise a substantially bowl shaped holding part 110A, having an upper rim 19 spaced apart over a small gap 115 from the ball surface, as shown in FIGS. 12B and C. To this end the rim 19 may be provided with a series of small, spaced apart notches 19C or the like, for defining the gap 115 and at the same time keeping the ball rotatably closed in the housing 110. This can have the advantage that once the product is picked up by the ball 7 it will not be scraped off by a seal. Thus even small amounts of product dispensed at a time will almost entirely be transferred to the surface 5 to be treated.

In the general embodiment of FIG. 12A the capsule 17 is pressed in an axial direction along the axis 13 into the housing 15. In the housing 15 a push rod 111 is provided, driven by any suitable means (not shown in FIG. 12A) such as but not limited to an electrical, pneumatic, hydraulic or magnetic motor, stepping motor, or by hand, for example by a screw knob external to the housing. The push rod 111 engages the side of the piston 109 facing outward from the reservoir 102, through the open end 107, preferably fitting into an indentation 112 in the piston, in order to properly center the piston and push rod. One or more light guides 113 can be positioned around the wall 106 of the reservoir, extending between a position close to the light source 9, here shown as a plurality of LED's 9A, and a position closed to or in abutment with the housing 110 of the capsule 17. Thus light from the light source 9, especially the LED's can be transferred to the capsule 17 by the light guide(s) passed the reservoir 102, unhindered by the product 3 in the reservoir 102, as shown by the arrows 90.

As can be seen in FIG. 12A the capsule 17 can be provided with a groove or cutouts 103, similar to the groove 103 shown in e.g. FIG. 1-5, for example at the transition between the part 110A and the peripheral wall 106 or below it, in which the light guide(s) 113 can hook, similar to the rim 150 of FIG. 1 or the fingers 52 in FIG. 6-11, for holding the capsule 17 in position and at the same time providing a proper placing of the ends 116 of the light guide(s) close to or in abutment with the housing 110 of the capsule 17. The light guides(s) can be resiliently flexible or can be mounted such that they can move partly outward in order to mount and release the cartridge 17 again. For example the light guide(s) can tilt, bend or translate to that end.

As can be seen in FIG. 12A a spring 117 can be provided below the cartridge, which can be loaded by placing the cartridge and/or by moving the piston 109 and rod 111 forward, such that at least when the piston 109 is near or at an end position, with the reservoir substantially empty, and the capsule 17 is released by the coupling means such as the light guide(s), the capsule is pushed out of the housing by the spring 117, at least in part, such that it can be more easily removed, for example by tilting the device 1 above a waste basket or the like, such that a user has to have no or only minimal contact with the used capsule.

FIG. 12 shows part of a casing or housing 15, with a applicator unit 104 carrying a capsule 17 with a cap 37, prior to use for dispensing. In this embodiment the unit 104 is represented with a cartridge similar to that of FIG. 12A and the unit 104 as such as shown in more detail in FIG. 13. In this embodiment the push rod 111 comprises a hollow cylinder 120 engaging the piston 109, and a rod portion 121 mounted on a spindle 122 of a motor 123. Within the cylinder 120 a spring 124 is provided, biasing the cylinder 120 away from the rod portion 121. The rod portion 121 is provided with two wing portions 125 extending side ways and sliding along sliding surfaces 126 in the casing 15, such that the rod portion 121 is prevented from rotation around the axis 13 and around the spindle 122. The rod portion is provided with internal screw threads 127 complementary to screw threads 128 on the spindle. Thus a rotation of the spindle 122 driven by the motor 123 in the right direction will axially move the rod portion and thus the push rod 111 as such, pushing the piston 109 into the reservoir 102. The spring 124 is resilient such that the piston 109 can be pushed up to against the wall 21, emptying the reservoir substantially completely. However, when the piston 109 has been moved into the end position the rod portion 121 can be moved slightly further in order to load the spring 124, such that when the capsule 17 is released it is pushed out by the spring 124.

Again upon placing the capsule 17 a switch can be operated for empowering the device, especially the light source 9 and/or the motor 123.

The general concept of a device 1 of FIG. 12 is also used in the embodiments shown in FIG. 13-15, be it with different constructions.

FIG. 13A shows in perspective view a device 1 in cross section, of which the capsule 17 is as discussed with reference to FIG. 12. In this embodiment however the coupling means between the capsule 17 and the housing 15 are arranged differently. In this embodiment the housing 15 or at least the unit 104 comprises an arm 129 pivotably mounted. The arm 129 has a hook 130 which can fit in a groove 103 in the capsule 17, especially near the transition between the wall 106 and the housing part 110A. The arm is biased by a spring 131, such that the hook 130 is forced into said groove 103. The opposite end 132 of the arm 129 can be pushed, such that the hook 130 is pivoted out of the groove 103. Then the capsule 17 can be released out of the housing 15, and as discussed before, be pushed out by the spring 124.

In FIG. 13A a cap 37 is mounted on the capsule 17, over the ball 7, wherein the cap 37 comprises, at a side facing the ball 7 a rim 38A forcing the ball 7 against the opening 108, especially against a sealing ring 108 around the opening 108. Thus the opening 108 is closed by the ball 7 as long as the cap 37 is mounted.

In the embodiment of FIG. 13 (which includes all of FIGS. 13A-H) the piston 109 has a face facing the opening 108 which is adapted to fit snugly against the wall 21, in order to minimize a rest volume of the reservoir 102 when the piston 109 is moved forward against the wall 21.

FIG. 13B-I shows a sequence of placing a capsule 17, dispensing the product 3 and removing the capsule 17 again. In FIG. 13B-I only the unit 104 and capsule 17 are shown.

FIG. 13B shows the rod portion 121 in a rearward end position (i.e. closest to the motor 123) and the capsule 17 with cap 37 held close to the inserting opening 15A of the housing 15 or at least of the unit 114. The piston 109 is also in the most rearward position, the volume of the reservoir 102 maximal. FIG. 13C shows the capsule during insertion into the opening 15A, the hook 130 sliding along the wall 106, biased against the wall 106 by the spring 131. In FIG. 13D the capsule 17 has been inserted maximally, such that the hook 130 can engage the groove 103, locking the capsule 17 in position. The rod 111 engages the piston 109, specially the indentation 112 therein. Then the cap 37 can be removed, as shown in FIG. 13E. Then the device 1 is ready for use.

By driving the motor 123 the piston is moved forward, dispensing the product 3 from the reservoir 102.

FIG. 13F shows the unit 104 with the capsule 17, with the piston 109 moved forward maximal by the motor, the reservoir empty. Then in FIG. 13G the motor 123 has been driven slightly further, such that the spindle 122 has moved the rod portion further forward, loading the spring 124. Then in FIG. 13H the arm is shown pivoted such that the hook 130 is pulled out of the groove 103, thus releasing the capsule 17. Thus the capsule 17 is pushed out of the housing 15 by the spring 124, as shown in FIG. 13I.

In FIG. 13 the light is guided through the light guides 113 alongside the reservoir 102 to the capsule 17, to be radiated out through the ball 7.

FIG. 14A shows an alternative embodiment of a unit 104 and capsule 17, in cross sectional perspective view, wherein the capsule again is substantially as shown and discussed in FIGS. 12 and 13. One difference is in a groove 103A in an outward facing side of the wall 106. In this embodiment the unit 104 has, as in the embodiments of FIGS. 12 and 13, a substantially cylindrical housing part 104A with a first end 104B forming the insertion opening 15A. In this embodiment the push rod 111 is substantially solid, with a bore containing internal screw threads 127 for cooperation with screw threads 128 on the spindle 122. Within the housing 104A, close to the first end 104B a guide element 133 is provided for receiving the capsule 17 or at least the reservoir 102 thereof. The guide element 133 can for example be substantially cylindrical, and has a ring shaped cross wall 134 with an opening 135 through which the push rod 111 can extend for engaging the piston 109. Spaced further apart from the end 104B in the unit 104 a further cross wall 136 is provided, through which the push rod 111 extends as well. A spring 137 is provided between the two cross walls 134 and 136, around the push rod 111. In the wall 138 of the guide element 133 a number of openings 171 is provided, containing each a ball element 139, which in the coupled position as shown in FIG. 14A extend into the groove 103A, locking the capsule inside the guide element 133, since the balls 139 cannot move outward in this position due to the wall of the unit 104.

As can be seen in FIG. 14A the wall 138 comprises a further opening 140, for example at a side of the cross wall 134 opposite the ball elements 139, into which a hook 130 of an arm 129 can engage when the guide element 133 has been pushed into the housing 104 maximally. The arm 129 is pivotally mounted in the wall of the unit 104, biased by a spring 141 such that the hook 130 is forced into the opening 140, locking the guide element 133 in position. In this position the spring 137 is loaded, biasing the guide element 133 and thus the capsule 17 outward of the housing 15, 104, in axial direction.

In an inward facing side of the wall of the housing 104A a groove 143 is provided, such that if the guide unit 133 is moved outward the balls 39 can move outward into the groove 143, releasing the capsule 17 from the guide element 133. Thus the capsule can be removed again.

In FIG. 14 (including all FIGS. 14A-I) the light source 9, such as LED's 9A can be provided for example at the cross wall 136, at least one light guide 113 being provided by or in the guide element 133. A switch 144 can be provided within the unit 104, such that the guide element 133 can operate the switch when being pushed into the housing 15. This switch 144 can thus switch the electrical circuit, for example the motor and/or the light source, such that if the capsule is not placed properly, the device or at least the light source 9 cannot be activated.

FIG. 14B shows a unit 104 with a capsule 17 spaced apart from the unit 104. As in the embodiment of FIG. 13 a cap 37 is placed over the ball 7, pushing the ball against the rim 108A closing the opening 108. In the housing 104A the guide element 133 is moved outward towards the end 104B, such that the balls 139 are received in the groove 143, such that the capsule 17 can be pushed into the guide element 133. The rod 111 is in a rearward position, the spring 137 relatively relaxed.

In FIG. 14C the reservoir of the capsule 17 is received in the guide element 133, such that an end thereof abuts the cross wall 134. In FIG. 14D the capsule 17 and guide element 133 are shown pushed further in, along the axis 13. Since the groove 143 has an inclined surface the balls 139 will be taken along with the guide element 133 and forced inward, into the groove 103A in the capsule 17, thus locking the capsule in the guide element 133. As is shown in FIG. 14D the arm 129 is pushed outward, such that the guide element 133 can pass to the position shown in FIG. 14E in which the hook 130 is pushed back, into the opening 140, locking the guide element 133 in this position. The spring 137 has been compressed and thus loaded. The switch 144 has been operated such that the device can be used. The push rod 111 engages the piston 109.

In FIG. 14F the push rod 111 and piston 109 are show in a position moved maximally forward by the motor 123 and spindle 122, such that the piston 109 engages the wall 21. Thus the reservoir has been emptied, the product 3 dispensed therefrom. If in this position the arm 129 is engaged, such that the hook 130 is pulled out of the opening 140, as is shown in FIG. 14G, the spring 137 will push the guide element 133 back outward to the end 104B, such that the balls 139 can move back into the groove 143, as shown in FIG. 14H. From this position the capsule 17 can be taken out of the guide element 133 and thus out of the housing 15, as shown in FIG. 14I.

FIG. 15A shows an embodiment in which the capsule 17 comprises a ring shaped reservoir 102 with a ring shaded piston 109. The push rod 111 in this embodiment is again carried and movable by a motor 123 with spindle 122, and has a substantially cylindrical end portion 111A, adapted to engage the piston 109. Central near an insertion opening 15A of the unit 114 a light source 109 is provided, schematically shown as a rectangle, which can again contain one or more light elements such as but not limited to LED's, which can during use emit light through the wall 21 and the ball 7. In this embodiment one or more openings 108 can be provided for connecting the reservoir 102 with the space 11B around part of the ball 7.

FIG. 15B shows an embodiment in which the light source 9 and the reservoir 102 are positioned in side by side relationship when the capsule is coupled to the unit 114 and/or the housing 15. In this embodiment the drive mechanism comprising the motor 123 and push rod 111 has been shown substantially as shown in FIG. 13, with a spring 124 between a rod portion 121 and a front end portion 120. However, also other constructions can be considered, including but not limited to as shown in FIGS. 12 and 14. In this embodiment the opening 108 is shown sideways from a central axis 13, but it could also be positioned on the axis 13. Coupling between the capsule 17 and the unit 114 or housing 15 can be achieved in any suitable way, for example one as discussed here before. Due to the asymmetric form only one position can be chosen for insertion, contrary to the previous embodiments in which the cartridges could be rotational symmetrical, at least as far as the coupling is concerned.

FIG. 15C shows an embodiment of a unit 114 substantially similar to that of FIG. 13, in which however the arm 129 has been positioned and designed differently, such that the rod portion 121 can engage an end of the arm opposite the hook 130, such that when the piston 109 has been moved forward such that the reservoir 102 has been emptied, the rod portion 121 contacts the arm 129 and that upon a further movement of the rod portion 121 towards the capsule 17 the spring 124 is loaded, as described before, and the arm 1209 is pivoted by the rod portion 121, releasing the hook 130 from the groove 103. Thus the capsule 17 is automatically released from the unit 114 and device 1.

FIGS. 16A and B disclose an embodiment of the present disclosure in which again a cartridge 17 is provided and a housing 15. This embodiment will be described mainly as far as it is different from the previous embodiments. The same or similar parts are indicated with the same or similar reference signs as used in FIG. 1-15. In this embodiment the cartridge 17 is inserted partly into an end of the housing 15, and can be connected thereto releasably in any suitable way, as for example discussed in the previous embodiments. In this embodiment lights 9, such as LED's are provided inside the housing 15, which can radiate light through part of the cartridge 17 towards a surface of skin (not shown). In FIG. 16B light rays 90 are shown schematically, partly passing along side the applicator element 7, here shown as a ball 7 a s discussed before. In this embodiment at least part of the light is irradiated on an area around the application zone 30 between the movable element 7 and the surface 5 such as the skin. Part of the light could pass through the applicator element 7 as well, if the element 7 is made transparent for said light. If different light frequencies are used, the applicator element could be made of a plastic material transparent for one or more of these frequencies but not for one or more other frequencies. Thus part of the light can pass through the ball and other another part of the light can only pass alongside the ball. Similarly the cartridge can at least partly be made of a material only transparent for part of the light used, such that a further part cannot pass through that part of the cartridge and for example can only exit the applicator through the applicator element, such as through the ball 7.

In this embodiment, as in the previous embodiments, the lights 9, 9A can be positioned directly near an end of the cartridge 17, or can be positioned further into the housing 15, wherein one or more light guides 113 can be provided for transferring the light from the light source 9, 9A to the cartridge 17.

A cartridge of the present disclosure could be provided with one or more light guides 113 for transferring light from a light source 9, 9A and/or light guides 113 in the housing to a specific area of the cartridge 17 for exiting the light to the skin and/or to the applicator element 7.

FIG. 17 discloses an embodiment of the present disclosure in which again a cartridge 17 is provided and a housing 15. This embodiment will be described mainly as far as it is different from the previous embodiments. The same or similar parts are indicated with the same or similar reference signs as used in FIG. 1-15. In this embodiment the cartridge 17 is inserted partly into an end of the housing 15, and can be connected thereto releasably in any suitable way, as for example discussed in the previous embodiments. In this embodiment light source 9, 9A can again be provided in or on the housing 15. In this embodiment the applicator element 7 is provided as a non-movable element provided at an outward facing end of the cartridge 17. The applicator element 7 is shown as a substantially smooth, curved element having a convex outer surface 30 forming a distribution zone. In this embodiment light guides 113 are shown extending alongside the reservoir 102 with exit ends 116 for the light close to the applicator element 7, preferably such that these ends 116 are covered by the element 7. An opening 108, here shown as a channel, connects the reservoir with the distribution zone 30 of the applicator element 7. During use the reservoir 102 is emptied by movement of the piston 109 forward, reducing the volume, preferably to about zero ml. The product 3 will be forced out of the opening 108 and by movement of the element 7 over the skin will be distributed, both over the surface 30 and over the skin.

In preferred embodiments at least part of the light emitted is passed through at least part of the cartridge 17. This can have the advantage that the cartridge can be used for influencing the light emitted, for example in direction, scattering, color, frequency, intensity and power and the like. This can for example provide for the possibility of using the same light source 9, especially the same LED's 9A for different products to be distributed, wherein the light frequencies and/or intensities of the light and/or the position(s) in which the light contacts the skin can be influenced, depending on the product to be dispensed and the interaction desired. The cartridge can in effect be used as a filter for the light.

Since in preferred embodiments of the present disclosure the applicator element will be substantially impervious for the product 3 and will not absorb said product, it is easily ensured that the limited quantity of product dispensed is indeed all distributed accurately over the skin. Since the drive means accurately dispense the product in said limited quantity this provides for a highly accurate system, with very little to no loss of active product 3. Since in the preferred embodiments of the present disclosure the applicator element 7 during application of the product onto the skin will substantially not deform, it will compress the skin such that it will provide for a contact zone having the skin elastically deform around part of said surface, and can provide for a more preferred massaging effect of the skin than when using a pliable element such as a sponge.

In preferred embodiments of the present disclosure preferably the only contact between the device and the skin onto which product is to be dispensed is provided for by the applicator element 7, which is part of a disposable cartridge 17. For example the light source(s) 9, 9A is/are shielded from such contact by at least part of the cartridge. Thus hygiene is improved and the device does not have to be cleaned as often as for example some of the prior art devices.

In the embodiments of the present disclosure preferably the cartridge can be released from the device without a user having to touch the cartridge, which again further improves hygiene. In the embodiments of the present disclosure preferably a mechanical drive is used for reducing the volume of the reservoir 102 and dispensing the product 3. This may improve accuracy of the movements and volume reduction over other drive means, such as magnetic, whereas a mechanical drive is economic and reliable and may prevent electro magnetic fields undesirable for a user.

A device 1 according to the disclosure can comprise a control unit 146, preferably connected to the motor 123, the light source 9 and/or a switch operated by placing the capsule 17 as discussed. The control unit can at least control the drive formed by or including the motor 123 for reducing the volume of the reservoir 102 to substantially zero milliliter, preferably in a single dispensing cycle of less then 15 minutes, especially of less than 5 minutes. The control can be set to have the drive reduce the volume of the reservoir 102 in one continuous step or intermittently, including a series of dispensing steps of seconds each. The control unit can for example be programmed to operate the motor 123 such that the piston 109 is driven forward into the reservoir for dispensing the product. The motor 123 can for example be driven such that the piston is driven forward intermittently, in steps, such that the product is dispensed in a number of quantities, for example equal portions, in a number of steps each having a predetermined duration. For example the control can be set to dispense $1/n^{th}$ of the volume of product 3 from the reservoir every X seconds, such that in n steps of X seconds all of the product is dispensed, whereas during each period the ball 7 can be rolled over the surface 5 for applying the product over a different portion of said surface. For example n could be between 1 and 50, for example between 4 and 20, such as for example between 8 and 15. In an test example n was chosen to be 12, whereas the duration X of each period was chosen to be 15 seconds. Thus all of the product 3 was dispensed in twelve periods of 15 seconds each. However, the duration of the period and/or the number of steps can be chosen as desired. In an embodiment the control unit 145 can be provided with the possibility to choose between different dispensing regimes or to set the number of steps and/or the duration thereof by a user.

A single dispensing cycle should be understood as a relatively short period in which a user dispensed the volume of product onto a relevant portion of his or her skin for a single treatment of said portion of the skin. For example for each such portion a different cartridge can be used or for the same portion of the skin for subsequent treatments, for example daily treatments, individual cartridges can be used.

The invention is by no means limited to the specific embodiments disclosed and described herein. Many variations are possible with in the inventive concept. For example the light source 9 can be provided at least partly in the cartridge 17, such that a specific light source can be provided for each cartridge, for example depending on the product to be dispensed. The cartridge can have a membrane as a movable wall part, in stead of a piston. Multiple openings could be provided for allowing product to be forced onto the applicator element. A cartridge could be connected to the housing 15 differently, for example such that it can be slid into the housing from a side, i.e. in a direction perpendicular to the longitudinal axis of the housing. In stead of a motor other means can be provided for reducing the volume of the reservoir, for example compressed gas, manually operated forcing means, a spring or the like.

These and similar amendments should be considered having been disclosed herein.

The invention claimed is:

1. A device for distributing, on a surface of a living body, a product containing an active component or forming a cosmetic product, the device comprising a housing and a cartridge, releasably coupled to the housing, wherein:

the cartridge comprises an applicator element and a portion that includes a reservoir containing said product and having a movable or deformable wall part for reducing the volume of the reservoir, wherein at least one opening is provided between the reservoir and the applicator element for applying the product to the applicator element by reducing the volume of the reservoir, the device is a self-contained, hand held device, the housing comprises at least one light source for radiating light through and/or alongside the cartridge and a drive for driving the movable and/or deformable wall part of the reservoir for reducing the volume of the reservoir; and the housing is provided with a front opening at a distal-most end of the housing, wherein the portion that includes the reservoir can be inserted through the front opening into the housing in an axial direction towards the drive.

2. A device of claim 1, wherein the applicator element is made of a material which is at least one of hard, rigid, impermeable for the product and non-absorbent for the product.

3. A device according to claim 1, wherein the cartridge is at least partly transparent for at least part of the light emitted by the light source.

4. A device according to claim 1, wherein the reservoir comprises a volume of product less than about 10 ml, wherein the movable and/or deformable wall is designed for reducing the volume of the reservoir to about zero and wherein the housing comprises a control unit for controlling at least the drive for reducing the volume of the reservoir.

5. A device according to claim 1, wherein the movable wall part is formed by or comprises a piston, wherein the drive comprises a mechanical drive including an electric motor or piezo motor.

6. A device according to claim 1, wherein the housing comprises a control unit for at least controlling the drive for reducing the volume of the reservoir to substantially zero milliliter, in a single dispensing cycle of less than 15 minutes, wherein the control is set to have the drive reduce the volume in one continuous step or intermittently, including a series of dispensing steps.

7. A device according to claim 1, wherein the device comprises at least one light guide for guiding the light from the at least one light source to an end of the light guide for transmitting the light to a surface of the skin and/or through the applicator element, wherein the or each light guide extends within the housing.

8. A device according to claim 1, wherein the applicator element is provided in and/or on the cartridge and the cartridge is provided in and/or on the housing such that during application to the skin contact between the device and the skin onto which product is to be dispensed is provided for by the applicator element only, which is part of the cartridge, wherein the cartridge is a disposable cartridge, and wherein a cartridge release system is provided with which the cartridge can actively be released and forced out of the housing without a user having to touch the cartridge.

9. A device according to claim 1, wherein at least one light guide is provided alongside at least part of said reservoir, guiding light from the light source passed the reservoir to the applicator element and/or to a position adjacent the applicator element.

10. A device for dispensing a product for skin treatment, wherein the device comprises a housing and a cartridge comprising an applicator element and a product reservoir, wherein the cartridge and the housing are provided with cooperating coupling elements for releasably coupling the cartridge to the housing such that the reservoir extends at least partly inside the housing, at least the applicator element extending at least partly outside the housing for engaging skin, wherein the cartridge comprises at least first coupling or linking means, for cooperation with second coupling or linking means provided in and/or on the housing, wherein said first coupling or linking means and second coupling or linking means are arranged for grasping each other to releasably fix the cartridge to the housing, wherein the device is a self-contained, battery operated, hand held device, and wherein at least one light guide is provided in the housing alongside at least part of said reservoir, guiding light from a light source provided in the housing passed at least part of the reservoir to the applicator element and/or to a position adjacent the applicator element, wherein the housing is provided with a front opening at a distal-most end of the housing, wherein the cartridge has a portion that includes the reservoir, wherein the portion that includes the reservoir can be inserted through the front opening into the housing.

11. A device according to claim 10, wherein the applicator element is a movable element.

12. A device according to claim 10, wherein the applicator element is a movable, non-deformable element, wherein the cartridge has a cartridge housing and a part of the applicator element extends outside the cartridge housing, wherein the reservoir is provided at a part of the cartridge housing spaced apart from the part of the applicator element extending outside the housing, wherein the reservoir has a movable wall part formed by a piston at a side facing away from the applicator element, for reducing the volume of the reservoir for forcing product from the reservoir onto the applicator element.

13. A device according to claim 12, wherein the cartridge housing has a part, which part is close to an end of the at least one light guide, the said at least one part of the cartridge housing being transparent for at least part of the light during use guided through the light guide, such that light can be transmitted through the cartridge from the light source inside the housing.

14. A device according to claim 13, wherein the applicator element is a ball, wherein the ball is transparent for at least part of the light guided by the at least one light guide and transmitted through said transparent part of the cartridge housing.

15. A device according to claim 10, wherein the housing comprises a mechanical drive comprising a motor and a drive rod movable by the motor, wherein the reservoir has a piston, said piston bounding part of the reservoir, the drive rod engaging said piston for moving the piston into the reservoir and thus reducing the reservoir volume, forcing product onto the applicator element, wherein a control unit is provided for controlling at least one of the drive and the at least one light source, at least for timing a dispensing cycle and automatically switching off the device after a dispensing cycle.

16. A device according to claim 15, wherein the control unit is provided for at least controlling the drive for reducing the volume of the reservoir to substantially zero milliliter in a single dispensing cycle of less than 15 minutes, wherein the control is set to have the drive reduce the volume in one continuous step or intermittently, including a series of dispensing steps of seconds each.

17. A device of claim 10, wherein the housing is provided with a switch, activated by placement of the cartridge into the housing, for switching on the device, and is deactivated when removing the cartridge, such that a drive element of the device can only be operated when a cartridge has been placed in the housing of the device.

18. A method for treatment of human skin, wherein a cartridge comprising a portion including a reservoir containing a product comprising an active skin treating component is mounted into a housing with a front opening at a distal-most end of the housing, wherein the portion that includes the reservoir is inserted through the front opening into the housing, wherein a drive in the housing is activated for reducing the volume of the reservoir, such that the product is forced out of the reservoir onto at least a first portion of a movable applicator element provided in and/or on the cartridge, wherein the movable applicator element is moved such that the at least first portion of the movable applicator element moves away from a first position where it was provided with product forced out of the reservoir towards a second position in which said first portion faces outwardly such as to allow that the product applied to said first portion of the movable applicator element can be applied to the skin to be treated, with which applicator element the product is distributed over a portion of the skin to be treated without being absorbed by the movable applicator element, wherein a self-contained, hand held and battery operated device is used, wherein during application light from a light source in the housing is emitted from the device onto the skin, for cooperating with the product dispensed in the treatment of the skin, wherein after application of the contents of the reservoir onto the skin the cartridge is removed from the housing and is discarded, including the movable application element, such that the cartridge can be replaced by a new cartridge, and wherein the light is guided by at least one light guide in the housing from the light source to the movable applicator element and/or the skin being treated.

19. A method according to claim 18, wherein the movable applicator element is a ball which during treatment of the skin is rolled over the skin, whereby the skin is compressed by the movable applicator element and the movable applicator element is substantially not deformed, wherein the light is radiated onto a portion of the skin deformed by the ball.

20. A method according to claim 18, wherein the movable applicator element is a ball which during treatment of the skin is rolled over the skin, whereby a portion of the ball is substantially the only contact between the device and the skin, and wherein the cartridge is discarded without being touched by a user.

21. A hand held device for distributing, on a surface of a living body, a product containing an active component or forming a cosmetic product, the device comprising a housing and a cartridge, releasably coupled to the housing, wherein:
  the device is a battery operated hand held device,
  the cartridge comprises an applicator element and a portion that includes a reservoir containing said product and having a movable or deformable wall part for reducing the volume of the reservoir, wherein at least one opening is provided between the reservoir and the applicator element for applying the product to the applicator element by reducing the volume of the reservoir,
  the housing comprises at least one light source for radiating light through and/or alongside the cartridge and a drive for driving the movable and/or deformable wall part of the reservoir for reducing the volume of the reservoir,
  the housing is provided with a front opening at a distalmost end of the housing, wherein the portion that includes the reservoir can be inserted through the front opening into the housing in an axial direction towards the drive, and
  the device comprises at least one light guide for guiding the light from the at least one light source within the housing to an end of the light guide for transmitting the light to a surface of the skin.

22. A hand held device according to claim 21, wherein the applicator element is made of a material which is at least one of hard, rigid, impermeable for the product, and non-absorbent for the product.

23. A device according to claim 6, wherein the volume of the reservoir is reduced in a single dispensing cycle of less than 5 minutes.

24. A device according to claim 16, wherein the volume of the reservoir is reduced in a single dispensing cycle of less than 5 minutes.

25. A device according to claim 11, wherein the applicator element is a ball.

26. A device according to claim 13, wherein the part is in contact with the at least one light guide.

27. A device for distributing, on a surface of a living body, a product containing an active component or forming a cosmetic product, the device comprising a housing and a cartridge, releasably coupled to the housing, wherein:

the cartridge comprises an applicator element, wherein the applicator element is a movable element, wherein the cartridge further comprises a reservoir containing said product and having a movable or deformable wall part for reducing the volume of the reservoir, wherein at least one opening is provided between the reservoir and the applicator element for applying the product to the movable element by reducing the volume of the reservoir, the device is arranged such that by reducing the volume of the reservoir the product is applied to at least a first portion of the movable element which first portion faces the at least one opening in a first position of the movable element, and such that upon moving the movable element the at least first portion of the movable element moves away from said first position towards a second position in which said first portion faces outwardly such as to allow that the product applied to said first portion of the movable element can be applied to the surface of the living body, the device is provided with a pump mechanism to act upon the movable or deformable wall part in order to ensure all of the product can be dispensed and control the rate and amount of product delivered, the device is a self-contained, hand held device, and the housing comprises at least one light source for radiating light through and/or alongside the cartridge and a drive for driving the movable and/or deformable wall part of the reservoir for reducing the volume of the reservoir.

28. A device according to claim 27, wherein the movable element is a ball.

29. A device for distributing, on a surface of a living body, a product containing an active component or forming a cosmetic product, the device comprising a housing and a cartridge, releasably coupled to the housing, wherein:

the cartridge comprises an applicator element and a portion that includes a reservoir containing said product and having a movable or deformable wall part for reducing the volume of the reservoir, wherein at least one opening is provided between the reservoir and the applicator element for applying the product to the applicator element by reducing the volume of the reservoir, the device is a self-contained, hand held device, the housing comprises at least one light source for radiating light through and/or alongside the cartridge and a drive for driving the movable and/or deformable wall part of the reservoir for reducing the volume of the reservoir, the cartridge comprises at least first coupling or linking means, for cooperation with second coupling or linking means provided in and/or on the housing, wherein said first coupling or linking means and second coupling or linking means are arranged for grasping each other to releasably fix the cartridge to the housing, and the housing is provided with a front opening at a distalmost end of the housing, wherein the portion that includes the reservoir can be inserted through the front opening into the housing.

30. A device according to claim 1, wherein the cartridge comprises at least first coupling or linking means, for cooperation with second coupling or linking means provided in and/or on the housing, wherein said first coupling or linking means and second coupling or linking means are arranged for grasping each other to releasably fix the cartridge to the housing.

31. A device according to claim 1, wherein the applicator element has a width that is larger than a width of the front opening of the housing.

* * * * *